(12) United States Patent
Towle et al.

(10) Patent No.: US 10,450,408 B2
(45) Date of Patent: Oct. 22, 2019

(54) METHOD FOR MAKING POLYARYLALIPHATICETHERKETONE POLYMERS AND COPOLYMERS THEREOF

(71) Applicant: KETONEX LIMITED, Oxford (GB)

(72) Inventors: Ian David Henderson Towle, Oxford (GB); Kaylie Jane Smith, Oxford (GB)

(73) Assignee: Ketonex Limited, Oxford (GB)

( * ) Notice: Subject to any disclaimer, the term of this patent is extended or adjusted under 35 U.S.C. 154(b) by 194 days.

(21) Appl. No.: 15/510,575

(22) PCT Filed: Sep. 10, 2015

(86) PCT No.: PCT/GB2015/052614
§ 371 (c)(1),
(2) Date: Mar. 10, 2017

(87) PCT Pub. No.: WO2016/038370
PCT Pub. Date: Mar. 17, 2016

(65) Prior Publication Data
US 2017/0253696 A1     Sep. 7, 2017

(30) Foreign Application Priority Data
Sep. 10, 2014    (GB) .................... 1415972.7

(51) Int. Cl.
| C08G 61/12 | (2006.01) |
| C08G 65/40 | (2006.01) |
| C07C 49/84 | (2006.01) |
| C07C 45/46 | (2006.01) |
| C08G 73/10 | (2006.01) |
| C08G 75/23 | (2006.01) |
| D01F 6/66  | (2006.01) |

(52) U.S. Cl.
CPC ............ *C08G 61/127* (2013.01); *C07C 45/46* (2013.01); *C07C 49/84* (2013.01); *C08G 65/40* (2013.01); *C08G 65/4012* (2013.01); *C08G 73/1071* (2013.01); *C08G 75/23* (2013.01); C08G 2261/122 (2013.01); C08G 2261/312 (2013.01); C08G 2261/334 (2013.01); C08G 2261/3323 (2013.01); C08G 2261/45 (2013.01); C08G 2650/40 (2013.01); *D01F 6/665* (2013.01)

(58) Field of Classification Search
CPC .. C08G 65/40; C08G 65/4012; C08G 61/127; C08G 75/23; C08G 73/1071; C07C 49/84; C07C 45/46; D01F 6/665
See application file for complete search history.

(56) References Cited

U.S. PATENT DOCUMENTS

| 3,065,205 A | 11/1962 | Bonner, Jr. |
| 3,288,855 A | 11/1966 | Schisla et al. |
| 3,953,400 A | 4/1976 | Dahl |
| 4,698,393 A | 10/1987 | Jansons et al. |
| 4,751,274 A | 6/1988 | Ittemann et al. |
| 4,777,282 A | 10/1988 | Towle |
| 4,786,694 A | 11/1988 | Clendinning et al. |
| 4,808,693 A | 2/1989 | Dahl et al. |
| 4,816,556 A | 3/1989 | Gay et al. |
| 4,820,792 A | 4/1989 | Towle |
| 4,837,284 A | 6/1989 | Matzner et al. |
| 4,841,011 A | 6/1989 | Towle |
| 4,841,013 A | 6/1989 | Towle |
| 4,843,131 A | 6/1989 | Becker et al. |
| 4,861,915 A | 8/1989 | Clendinning et al. |
| 4,898,983 A | 2/1990 | Towle |
| 4,912,181 A | 3/1990 | Becker et al. |
| 4,959,424 A | 9/1990 | Matzner et al. |
| 4,960,555 A | 10/1990 | Satake et al. |
| 4,990,589 A | 2/1991 | Towle et al. |
| 5,084,530 A | 1/1992 | Matzner et al. |
| 5,116,933 A | 5/1992 | Newton |
| 5,145,938 A | 9/1992 | Towle |
| 5,221,728 A | 6/1993 | Bennett |
| 5,260,404 A | 11/1993 | Whiteley et al. |
| 5,338,821 A | 8/1994 | Towle |
| 5,734,005 A | 3/1998 | Daniels et al. |
| 5,969,082 A | 10/1999 | Kuwahara et al. |
| 6,316,660 B1 | 11/2001 | Sato et al. |
| 6,437,080 B1 | 8/2002 | McGrail |
| 9,023,468 B2 | 5/2015 | Towle |
| 9,683,079 B2 | 6/2017 | Pratte |

(Continued)

FOREIGN PATENT DOCUMENTS

| CN | 102 875 819 A | 1/2013 |
| EP | 174 207 A2 | 3/1986 |

(Continued)

OTHER PUBLICATIONS

H. M. Colquhoun, et al., "Polyetherketones based on para-carborane: synthesis, sulfonation, and membrane-forming characteristics," Polymer vol. 38, No. 17, pp. 4539-4546, 1997.

(Continued)

*Primary Examiner* — Shane Fang

(74) *Attorney, Agent, or Firm* — Knobbe, Martens, Olson & Bear, LLP

(57) ABSTRACT

A process for producing a polymer includes polymerizing a monomer system containing a compound of formula: Ar—O—Ar—C(=O)—X—C(=O)—Ar—O—Ar in a reaction medium containing a Lewis acid. In the formula, X is an aliphatic moiety, and Ar is an aromatic moiety. The reaction medium further includes a dielectrophile. The dielectrophile is a compound of formula: L-(O=)C—Ar—C(=O)-L, in which L is a leaving group.

13 Claims, No Drawings

(56) References Cited

U.S. PATENT DOCUMENTS

| | | |
|---|---|---|
| 9,765,185 B2 | 9/2017 | Louis et al. |
| 9,783,636 B2 | 10/2017 | Chaplin |
| 2007/0031371 A1 | 2/2007 | McManus et al. |
| 2009/0082538 A1 | 3/2009 | Wu |
| 2010/0234539 A1 | 9/2010 | Malet |
| 2011/0178237 A1 | 7/2011 | Ono et al. |
| 2012/0263953 A1 | 10/2012 | Podobinski et al. |
| 2014/0235787 A1 | 8/2014 | Capra et al. |
| 2015/0322210 A1 | 11/2015 | Sriram |
| 2015/0337082 A1 | 11/2015 | Pratte |
| 2016/0152769 A1 | 6/2016 | Wilson |
| 2017/0010323 A1 | 1/2017 | Towle |
| 2017/0253696 A1 | 9/2017 | Towle |

FOREIGN PATENT DOCUMENTS

| | | |
|---|---|---|
| EP | 0 254 585 A2 | 1/1988 |
| EP | 0 262 919 A2 | 4/1988 |
| GB | 2287031 A | 9/1995 |
| WO | WO 86/02368 A1 | 4/1986 |
| WO | WO 89/04848 A1 | 6/1989 |
| WO | WO 90/00573 A1 | 1/1990 |
| WO | WO 9207894 A1 | 5/1992 |
| WO | WO 02/00270 A1 | 1/2002 |
| WO | WO 2011/004164 A2 | 1/2011 |
| WO | WO 2014/095794 A2 | 6/2014 |

OTHER PUBLICATIONS

H. M. Colquhoun, et al., "Polyetherketones from diarylcarboranes: a new approach to semi-inorganic polymers," Polymer vol. 38, No. 10, pp. 2447-2453, 1997.

International Search Report mailed by European Patent Office dated Nov. 11, 2015 in the corresponding PCT Application No. PCT/GB2015/052614.

Written Opinion mailed by European Patent Office dated Nov. 11, 2015 in the corresponding PCT Application No. PCT/GB2015/052614.

Ö. Özarslan, et al., "Novel poly(arylene ether ketone ketone)s synthesized by Friedel-Crafts acylation," Macromol. Chem. Phys, vol. 199, pp. 1887-1893, 1998.

J. Choi, et al., Effect of Endgroup Modification on Dynamic Viscoelastic Relaxation and Motion of Hyperbranched Poly(ether ketone)s, Journal of Polymer Science, Part B, Polymer Physics, vol. 46(19), pp. 2079-2089, 2008.

Search Report under Section 17(5) mailed by British Intellectual Property Office dated Mar. 11, 2015 in the corresponding British patent application No. GB1415972.7.

Chemical Abstract AN 1930:44191.

Chemical Abstract AN 1930:44192.

Chemical Abstract AN 1963:441388.

Chemical Abstract AN 1963:441387.

Chemical Abstract AN 2003:61487.

M. G. Zolotukhin, et al., "Superacid-Catalyzed Polycondensation of Acenaphthenequinone with Aromatic Hydrocarbons," Macromolecules, vol. 38, pp. 6005-6014, 2005.

Amendment to Search Report mailed by British Intellectual Property Office dated Sep. 2, 2015 in the corresponding British patent application No. GB1415972.7.

P. J. Horner, et al., "Aromatic Ether-Ketone-'X' Polymers," J. Mater, Chem., vol. 1(2), pp. 271-280, 1991.

Corfield, G.G., et al., Synthesis and Calorimetric Curing Study of Amino-Terminated Peek Oligomers, Journal of Polymer Science 30(5):845-849, Apr. 1, 1992.

Database WPI, Week 201343, Thomson Scientific, London, GB, Jan. 16, 2013, XP002742495.

Ding, N., et al, Novel Soluble Aromatic Poly(ether amide sulfone amide ether ketone ketone)s by Eletrophilic Solution Polycondensation, High Performance Polymers, 23(2):132-140, Mar. 1, 2011.

Huang, B., et al., Synthesis and Properties of Novel Random Copolymers of (polyether ketone ether ketone ketone)-poly(ether ketone imide) Journal of Polymer Research 20(81):1-8, 2013.

Noiset., O., et al., Surface Modification of Poly(aryl ether ether ketone) (PEEK) Film by Covalent Coupling of Amines and Amino Acides Through a Spacer Arm, Journal of Polymer Science 35(17):3779-3790, Dec. 1, 1997.

Search Report received in British Patent Application No. 1409128.4 dated Nov. 25, 2014.

Search Report received in British Patent Application No. GB1409126.8 dated Nov. 24, 2014.

Search Report received in connection with International Patent Application No. PCT/GB2010/001318 dated Mar. 29, 2011.

Search Report received in connection with International Patent Application No. PCT/GB2015/051488, dated Jul. 31, 2015.

Search Report received in International Patent Application No. PCT/GB2015/051487 dated Jul. 28, 2015.

Written Opinion received in connection with International Patent Application No. PCT/GB2015/051488, dated Jul. 31, 2015.

Written Opinion received in International Patent Application No. PCT/GB2015/051487 dated Jul. 28, 2015.

METHOD FOR MAKING POLYARYLALIPHATICETHERKETONE POLYMERS AND COPOLYMERS THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention concerns polyarylaliphaticetherketones (also known as polyaromaticaliphaticetherketones) (PAAEKs) which comprise aliphatic units in the polymer chain, e.g. between ketone units. In particular, it concerns methods for making the PAAEK polymers, copolymers and the required monomers thereof and methods for adding additional functionality to the polymers and copolymers.

Description of the Related Art

Common terminology involves naming polyaryletherketones (PAEKs) by reference to the structure of the repeating unit (as is standard in polymer chemistry) with family members being named according to the sequence of ether (symbolised by "E") and ketone (symbolised by "K") linkages in the repeat units where the E and K groups are separated by organic moieties. For example, polymers consisting essentially of the "EKK" repeating unit: —Ar—O—Ar—C(═O)—Ar—C(═O)— would be referred to as "PEKK". Copolymers comprising such an EKK repeat unit, together with, for example, a sulphone-containing unit, would be referred to as a PEKK-sulphone copolymer. For ease of notation the monomer 4,4'-diphenoxybenzophenone (used in the synthesis of PEKEKK) is referred to as "EKE" while 4,4'-bis(4-phenoxybenzoyl)benzene (used in the synthesis of PEKK) is referred to as "EKKE".

This terminology is extended for the PAAEK polymers and copolymers described herein so as to include the chain length of the aliphatic unit incorporated. By way of example, a polymer denoted as PEK10KEKK would have a —{CH$_2$—}$_{10}$— unit incorporated in the repeating unit, and PEK8KEKK-PEK6KEKK would be a copolymer having both a —{CH$_2$—}$_8$— and —{CH$_2$—}$_6$— aliphatic units in the polymer. As previously, for ease of notation the aliphatic monomers are abbreviated to the form EKXKE where X is the aliphatic unit. For example the monomer 4,4'-bis(4-phenoxybenzoyl)-1,10-decane

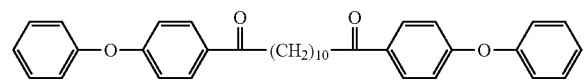

is abbreviated to EK10KE, and likewise, the monomer 4,4'-bis(4-phenoxybenzoyl)-1,6-hexane

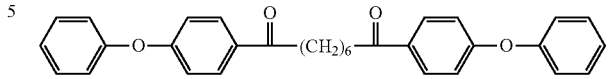

is abbreviated to EK6KE. Where the aliphatic unit is cycloaliphatic such as cyclohexyl

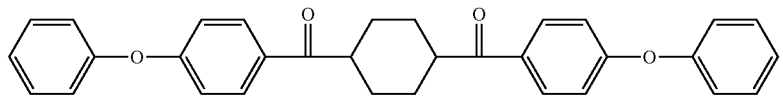 [SMILES: O=C(c1ccc(Oc2ccccc2)cc1)C1CCC(C(=O)c2ccc(Oc3ccccc3)cc2)CC1]

the abbreviation is EKcyclohexylKE.

Polyaryletherketones (PAEKs) have a variety of useful properties, such as excellent electrical insulating and mechanical properties at high temperature, high strength, toughness and resistance to heat, moisture and chemicals. Such polymers may be amorphous or semi-crystalline. Both types usually exhibit high glass transition temperatures ($T_g$), while the semi-crystalline forms also exhibit high melting temperatures ($T_m$). By way of their excellent mechanical and thermal properties, chemical inertness and resistance to stress cracking, these polymers are of particular interest for use in biomedical, aerospace, automotive, oil and gas, gears, bearings, electrical, composite and additive layer manufacturing applications.

Similarly, the polyarylaliphaticetherketones (PAAEKs) also have a variety of useful properties encompassing excellent electrical and mechanical properties, good/excellent toughness and resistance to chemicals, including moisture, at a range of temperatures. These properties vary in accordance with the degree of aliphatic nature of the PAAEKs. Some of these materials overlap the electrical, mechanical and physical properties of the nylons. However, they differ in that they are more resistant to hydrolysis and the subsequent degradation of properties that is common with the nylon family of materials in the presence of moisture. As with the PAEKs, the PAAEKs may also be amorphous or semi-crystalline. Applications include aerospace, electronics, automotive, medical, other industrial and additive layer manufacturing.

While some PAAEKs have been previously produced, these were found to be of low molecular weight and to exhibit poor stability during melt processing. The present inventors have found that problems with molecular weight control could be due to the use of aliphatic diacid chlorides in preparation, these being very air (moisture) sensitive and thus susceptible to hydrolysing back to the di-carboxylic acid, which is unreactive. Surprisingly, it has been found that by incorporating the aliphatic units via the novel Ar—O—Ar—C(═O)—X—C(═O)—Ar—O—Ar, EKXKE, monomers, the resulting polymers can be synthesised to high molecular weight and are stable during melt processing. The present disclosure therefore avoids the problems associated with aliphatic diacid chlorides by incorporating diaryl ethers on each end, thus producing EKXKE monomers that are air and moisture stable and easily manipulated. By way of example, if X═—{CH$_2$}$_8$—, then the monomer Ar—O—Ar—C(═O)—{CH$_2$}$_8$—C(═O)—Ar—O—Ar would be denoted as EK8KE.

The new PAAEK materials herein disclosed offer users a new platform of materials where the properties and performance of the materials can be tailored to specific needs, requirements and applications, by changing the length and nature of the aliphatic units. A further advantage is that the new PAAEK materials may be copolymerised as block or random copolymers, with a wide variety of other aromatic and/or aliphatic moieties comprising sulphone, imide, amide etc. to further widen the scope of potential properties and applications. In another aspect of the invention, the PAAEK materials may be functionalised to impart chemical reactivity into the polymer, such as via the incorporation of amine functionality. This amine functionality may be situated at either end of a linear polymer, on the branch ends of a branched polymer or may be distributed along the polymer chain.

SUMMARY OF THE INVENTION

The present inventors have thus found a method for producing the novel compounds (monomers) of general formula Ar—O—Ar—C(=O)—X—C(=O)—Ar—O—Ar (EKXKE) where X is an aliphatic moiety as herein defined, which can be used as monomers in polymerisation reactions to produce high molecular weight, melt stable polyarylaliphaticetherketone (PAAEK) polymers and copolymers.

Thus, viewed from a first aspect, the present invention provides a process for producing a polymer, said process comprising polymerising a monomer system comprising a compound of formula: Ar—O—Ar—C(=O)—X—C(=O)—Ar—O—Ar in a reaction medium comprising a Lewis acid where:

X is an aliphatic moiety
and
Ar is an aromatic moiety.

DETAILED DESCRIPTION OF THE INVENTION

Preferably, the reaction medium further comprises an electrophile (i.e. a compound comprising a nucleophilic leaving group) and thus the process for producing a polymer of the invention preferably involves the reaction of a nucleophile (EKXKE) with an electrophile. The electrophile is preferably a dielectrophile, especially a compound of formula: L-(O=)C—Ar—C(=O)-L (KK), where L denotes a leaving group, such as "Hal" (i.e. F, Cl, Br, I) or other leaving groups such as tosyl. Other suitable leaving groups will be evident to those skilled in the art. The compound of formula: Ar—O—Ar—C(=O)—X—C(=O)—Ar—O—Ar (EKXKE) can be viewed as a dinucleophile. More than one compound of formula: Ar—O—Ar—C(=O)—X—C(=O)—Ar—O—Ar (i.e. ones with differing X or Ar moieties) may be used in the process.

The polymer produced may be denoted by the abbreviation PEKXKEKK where the EKXKE comes from the dinucleophile and the KK from the dielectrophile. For example, the polymer produced from the monomers EK10KE and terephthaloyl chloride (KK) (a Hal-(O=C)—Ar—(C=O)-Hal monomer) may be denoted as PEK10KEKK.

In some aspects, both the nucleophile and electrophile may be multifunctional e.g. tri- or tetra- (or more) functional, for example 1,3,5-benzenetricarbonyl chloride, to give crosslinked or branched products. In another aspect, one of the comonomers may be self-polymerising in that one end of the molecule is a nucleophile and the other an electrophile, for example 4-phenoxybenzoyl chloride.

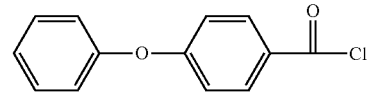 [SMILES: O=C(Cl)c1ccc(Oc2ccccc2)cc1]

Additional comonomers, nucleophiles and/or electrophiles, that may or may not have aliphatic nature, may be included in the monomer system to give random or block copolymers that may be semi-crystalline or amorphous.

The polymerisation takes place in a reaction medium comprising a Lewis acid to promote the reaction between the electrophile and the nucleophile and either a Lewis base controlling agent or a dispersion producing controlling agent.

As noted above, the novel compound of formula Ar—O—Ar—C(=O)—X—C(=O)—Ar—O—Ar (EKXKE), enables the production of the high molecular weight, melt stable polymers of the invention. Without wishing to be bound by theory, it is thought that the electron withdrawing nature of the ketone —C(=O)— ("K") units in the EKXKE monomers contribute to more stable polymers when compared to PAAEKs synthesised using diphenylether and an appropriate dielectrophile. Compounds of formula Ar—O—Ar—C(=O)—X—C(=O)—Ar—O—Ar (EKXKE) are made by the novel processes described herein, e.g. involving reaction of diphenyl ether with a dicarboxylic acid of X, where the diphenyl ether is in excess. This allows the easy purification of the EKXKE compound, and the central ketones partially deactivate the para carbons to electrophilic attack. The fact that the compound is easily purified contributes to the high molecular weight of the polymer. These compounds and processes for their preparation form a further aspect of the present invention.

X in the compounds (monomers) of formula Ar—O—Ar—C(=O)—X—C(=O)—Ar—O—Ar (EKXKE) and in the polymer repeat unit —Ar—O—Ar—C(=O)—X—C(=O)—Ar—O—Ar—C(=O)—Ar—C(=O)— (PEKXKEKK) is an aliphatic moiety, i.e. a moiety comprising aliphatic groups such that X is attached to the ketone carbons via a carbon atom. Preferably X is selected from saturated, optionally substituted, straight chain, cyclic and/or branched hydrocarbon moieties, especially saturated hydrocarbon moieties. Especially preferably, X is selected from cyclohexyl and —{CH$_2$}$_n$—, where n is an integer from 1 to 100, preferably 2 to 50, most preferably 2 to 22, preferably 2 to 18 or 2 to 12, especially, 3 to 10, e.g. 3, 4, 5, 6, 8 or 10. Where X is a substituted aliphatic moiety, one or more of the hydrogen atoms in the aforementioned groups may be replaced by halogens and/or hydrocarbyl e.g. alkyl groups.

Preferred dinucleophilic monomers may include all the EKXKE monomers listed below, i.e. the compound of formula Ar—O—Ar—C(=O)—X—C(=O)—Ar—O—Ar is preferably one or more selected from the following non-exclusive list:

TABLE 1

| Structure | Name |
|---|---|
| Ph-O-C6H4-C(O)-(CH2)2-C(O)-C6H4-O-Ph | EK2KE |
| Ph-O-C6H4-C(O)-(CH2)3-C(O)-C6H4-O-Ph | EK3KE |
| Ph-O-C6H4-C(O)-(CH2)4-C(O)-C6H4-O-Ph | EK4KE |
| Ph-O-C6H4-C(O)-(CH2)5-C(O)-C6H4-O-Ph | EK5KE |
| Ph-O-C6H4-C(O)-(CH2)6-C(O)-C6H4-O-Ph | EK6KE |
| Ph-O-C6H4-C(O)-(CH2)8-C(O)-C6H4-O-Ph | EK8KE |
| Ph-O-C6H4-C(O)-(CH2)10-C(O)-C6H4-O-Ph | EK10KE |
| Ph-O-C6H4-C(O)-(CH2)12-C(O)-C6H4-O-Ph | EK12KE |
| Ph-O-C6H4-C(O)-(CH2)20-C(O)-C6H4-O-Ph | EK20KE |
| Ph-O-C6H4-C(O)-(CH2)22-C(O)-C6H4-O-Ph | EK22KE |
| Ph-O-C6H4-C(O)-(C6H10)-C(O)-C6H4-O-Ph | EKCyclohexylKE |

The above compounds where one or more of the phenyl groups are replaced with any Ar group as herein defined are also encompassed.

Mixtures of the monomers may be used to give PAAEK copolymers containing two or more different aliphatic units. For example, using EK6KE and EK12KE would give a PEK6KEKK-PEK12KEKK random or block copolymer.

Where the dinucleophile EKXKE monomers are combined with any other dinucleophile monomers and suitably polymerised (i.e. where more than one type of EKXKE monomer is used), then the resulting copolymers may be random, block, semi-crystalline or amorphous.

Other monomers, for example non-aliphatic dinucleophile monomers, may be used in conjunction with the EKXKE monomers when synthesising random and/or block copolymers. Thus, in a preferred aspect, the reaction medium further comprises one or more comonomers, especially non-aliphatic and/or dinucleophilic comonomers, preferably selected from the following:

TABLE 2
| Structure | Label |
|---|---|
| 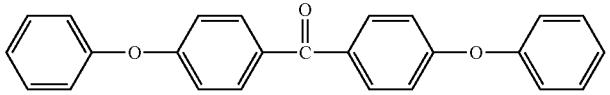 | EKE |
| 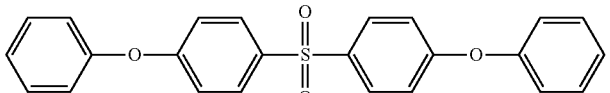 | ESE |
| 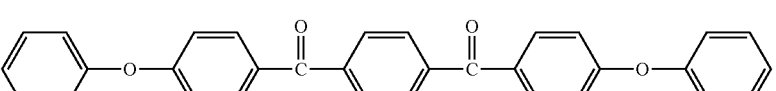 | EKKE |
| 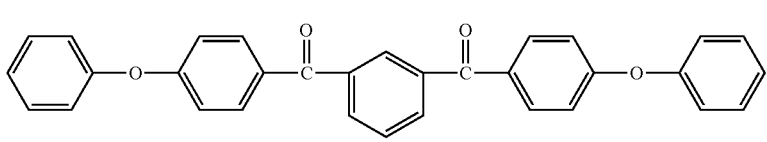 [SMILES: O=C(c1ccc(Oc2ccccc2)cc1)c1cccc(C(=O)c2ccc(Oc3ccccc3)cc2)c1] | EK-1,3-KE |
| 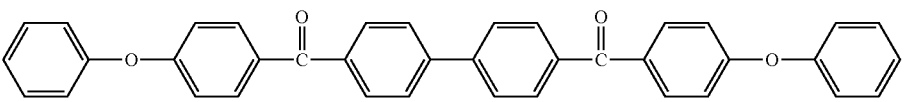 [SMILES: O=C(c1ccc(Oc2ccccc2)cc1)c1ccc(-c2ccc(C(=O)c3ccc(Oc4ccccc4)cc3)cc2)cc1] | EKBPKE |
| 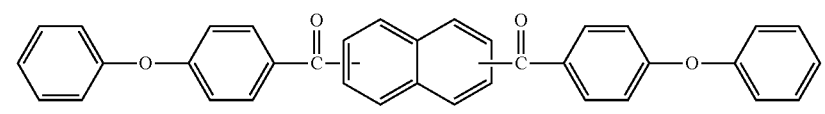 | EKNKE |
| 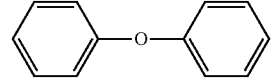 [SMILES: c1ccc(Oc2ccccc2)cc1] | DPE |
| 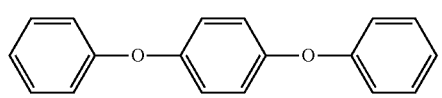 | DPB |
| 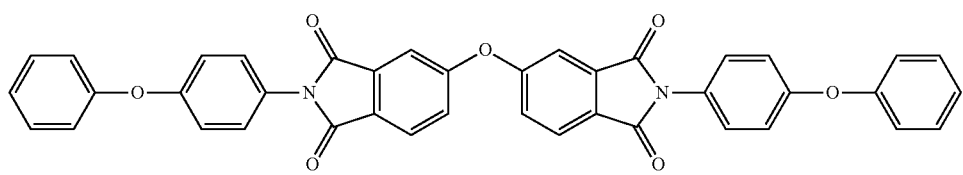 [SMILES: O=C1c2ccc(Oc3ccc4c(c3)C(=O)N(c3ccc(Oc5ccccc5)cc3)C4=O)cc2C(=O)N1c1ccc(Oc2ccccc2)cc1] | EIEIE |
| 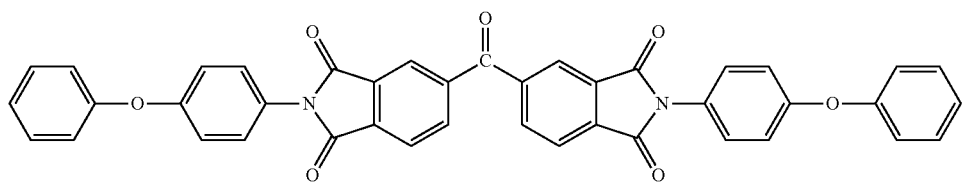 [SMILES: O=C(c1ccc2c(c1)C(=O)N(c1ccc(Oc3ccccc3)cc1)C2=O)c1ccc2c(c1)C(=O)N(c1ccc(Oc3ccccc3)cc1)C2=O] | EIKIE |
| 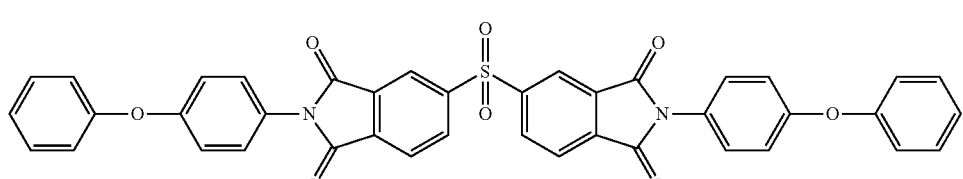 | EISIE |
| 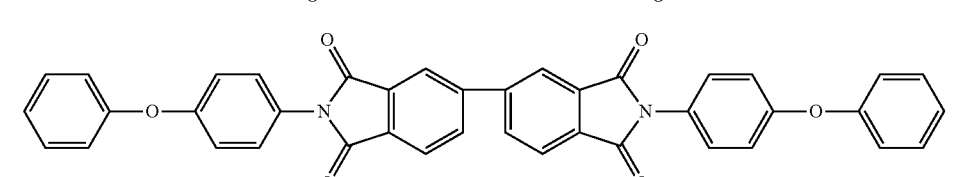 | EI-IE |

TABLE 2-continued

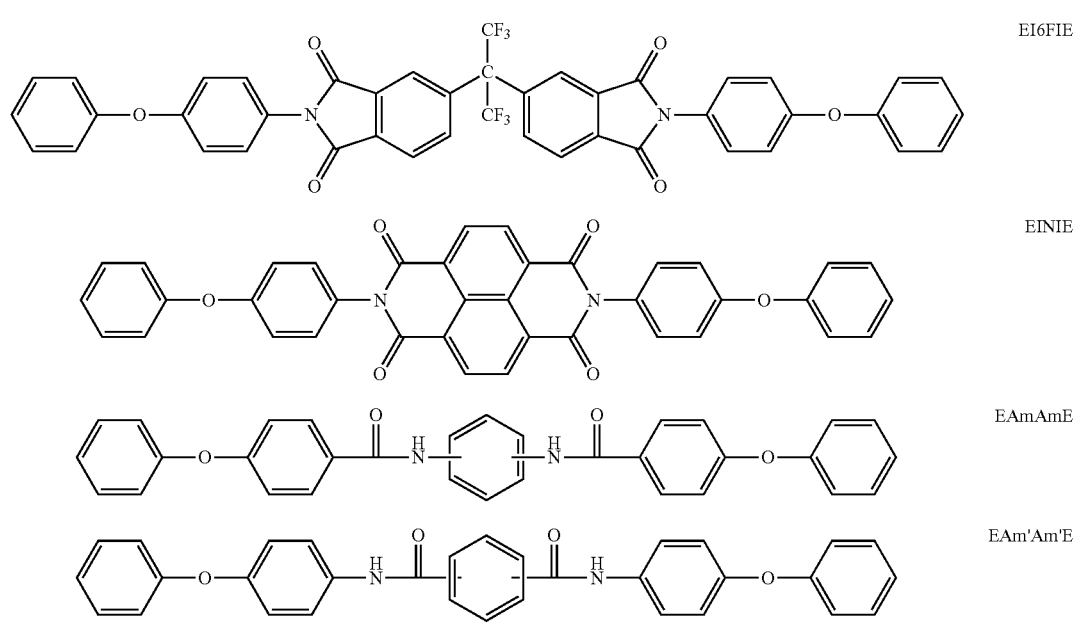

| | |
|---|---|
| | EI6FIE |
| | EINIE |
| | EAmAmE |
| | EAm'Am'E |

The above compounds where one or more of the phenyl groups are replaced with any Ar group as herein defined are also encompassed.

Other suitable nucleophile aliphatic containing monomers such as bibenzyl may be incorporated.

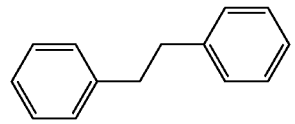

Preferred electrophile, (e.g. dielectrophile) monomers may include iso- and terephthaloyl halides (1,3- and 1,4-substituted respectively), orthophthaloyl halides (1,2-substituted), preferably iso- and terephthaloyl halides, preferably chlorides.

Especially preferred are the following Hal-C(=O)—Ar—C(=O)-Hal dielectrophile monomers:

TABLE 3

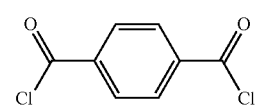
TPC

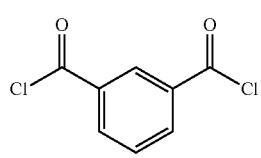 [SMILES: O=C(Cl)c1cccc(C(=O)Cl)c1]
IPC

TABLE 3-continued

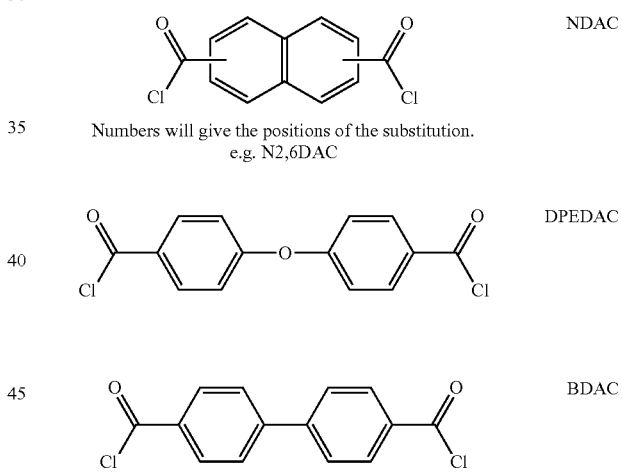

| | |
|---|---|
| | NDAC |
| | DPEDAC |
| | BDAC |

Numbers will give the positions of the substitution.
e.g. N2,6DAC

The above compounds where one or more of the phenyl groups are replaced with any Ar group as herein defined are also encompassed.

Whilst the above-listed chlorides are preferred, other acid halides, particularly the fluorides and the bromides, may also be used. Generally, the chlorides are preferred due to their availability, cost and reactivity. Other groups that are potentially displaceable under Friedel-Crafts conditions may also be used. These might include groups such as —OR, where R is methyl, ethyl, tosyl, isopropyl or other lower alkyl.

In some aspects, the process for producing a polymer may involve self-polymerising monomers (having both nucleophilic and electrophilic ends). Such preferred monomers include the following (and their analogues in which one or more of the phenyl groups are replaced with any Ar group as herein defined):

TABLE 4

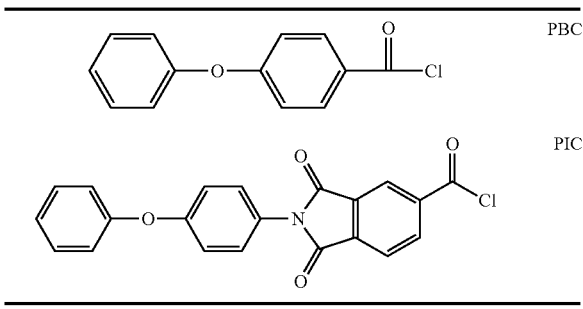

Crosslinked or branched polymers can be produced by including a multifunctional monomer in the polymerisation reaction medium. A multifunctional monomer may be electrophilic, nucleophilic, or may comprise both nucleophile and electrophile character in the same molecule. A mixture of these multifunctional monomers may be used.

Where branched units are present, they are preferably present in a molar percentage of 0.5% to 25% (i.e. 0.5 to 25M %).

Preferred examples of multifunctional monomers include:

TABLE 5

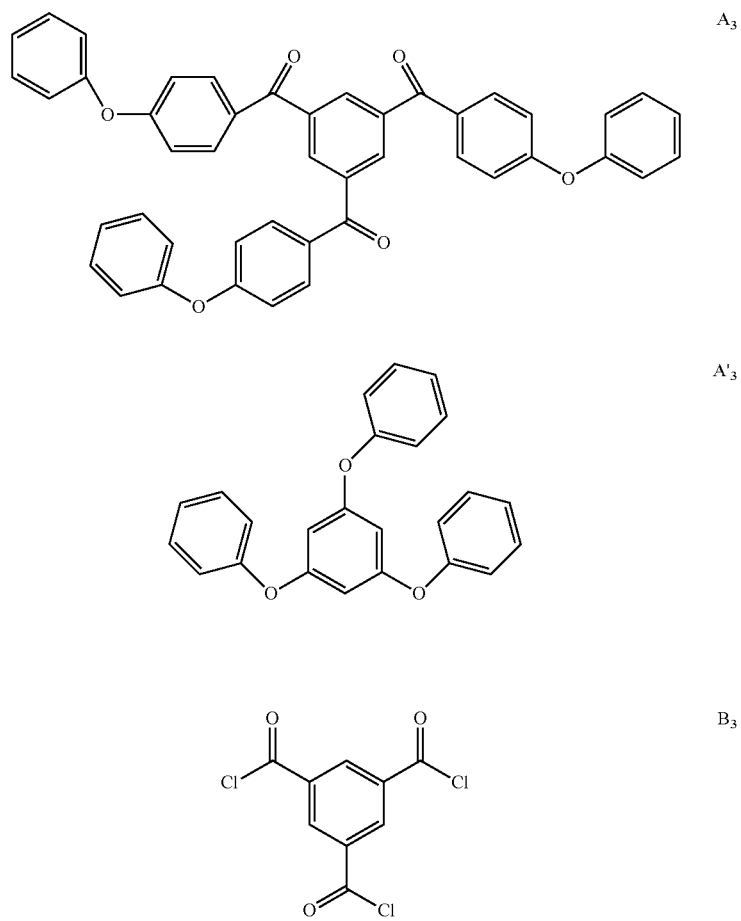

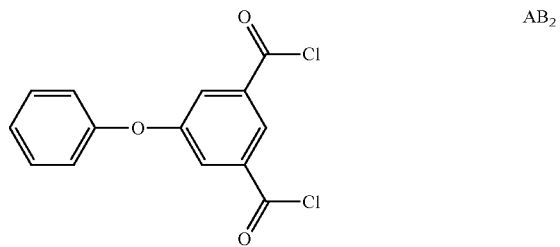

TABLE 5-continued

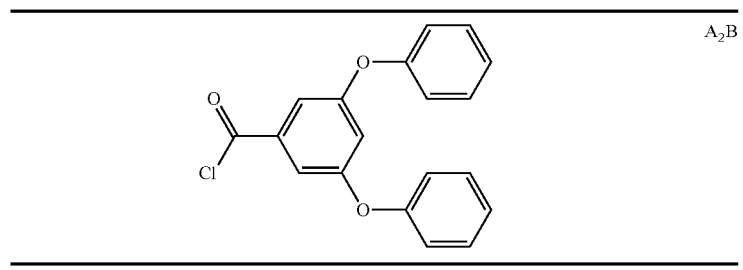

A₂B

The combinations of monomers suitable for producing the polymer materials herein described would be readily apparent to a person skilled in the art, as would the relative proportions of the monomers.

The proportion of 1,4-linked aromatic (e.g. phenyl) rings in the PAAEKs greatly influences the characteristics of the resulting polymer or copolymer (e.g. their processability, glass transition temperature ($T_g$) and its crystalline melting point ($T_m$), even to the extent of producing an amorphous PAAEK or copolymer thereof etc.) and the size and nature of the particles formed. Depending on the intended use for the polymer produced, the characteristics can be modified by changing the proportion of 1,4-linked aromatic rings in the polymer. This may be achieved by the use of monomers comprising 1,3-substituted aromatic rings. For example, isophthaloyl halides such as isophthaloyl chloride can be used as dielectrophile monomers, and the amounts chosen in relation to the other monomers in order to produce a polymer with the desired characteristics. Preferably the monomers are chosen such that the proportion of 1,3-linked aromatic rings in the resulting polymer is 0 to 100%, more especially 5 to 50%, particularly 20 to 40%, e.g. about 30%. All percentages and ratios are by mole ratio unless otherwise specified. The proportion of terephthaloyl (1,4-, tere-, or "T") to isophthaloyl (1,3-iso-, or "I")-linked aromatic rings in the resulting polymer can also be represented as a tere-:iso-, or "T:I" ratio and is preferably within the range of 100:0 to 0:100.

Particularly preferably the process comprises reacting any Ar—O—Ar—C(=O)—X—C(=O)—Ar—O—Ar (EKXKE) with terephthaloyl halide and/or isophthaloyl halides, preferably in a 1:1 ratio by weight. This would produce a 50:50 terephthaloyl:isophthaloyl PEKXKEKK polymer.

Preferably, all of the nucleophile monomers in the reaction mixture are of formula Ar—O—Ar—C(=O)—X—C(=O)—Ar—O—Ar. However, other nucleophilic monomers may also be present, e.g. dinucleophiles or multi-nucleophiles. Preferably, 1 to 100 molar percent of the nucleophile monomers in the reaction mixture are of formula Ar—O—Ar—C(=O)—X—C(=O)—Ar—O—Ar, especially 10 to 100, e.g. at least 30%, especially preferably at least 50%.

The molar ratio of nucleophiles to electrophiles may be in any range, provided both are present, however, preferably the range 99:1 to 1:99, e.g. 70:30 to 30:70, especially around 50:50 (i.e. 1:1). Multi-functional electrophiles may be included in the total electrophile component. The above is also applicable to oligomers.

High molecular weight (or very high molecular weight) products result when the ratio of nucleophile to electrophile monomers approach equivalence, e.g. 1:1. In order to control the molecular weight, such as where there is a need to control melt viscosity, this ratio is preferably in the range 100:80 to 80:100, more preferably between 100:90 to 90:100 and most preferably between 100:95 and 95:100. These ratios are often referred to as "out of balance" (OOB). Thus a polymerisation conducted in the ratio 100:98, or 98:100 would be 2% OOB. One makes the oligomers by running the reactions at high out of balance ratios, e.g. 10% OOB to 25% OOB.

The properties of the resultant polymer can be very significantly changed by changing the nature of X in the EKXKE monomer. Especially preferably, X in the compound of formula Ar—O—Ar—C(=O)—X—C(=O)—Ar—O—Ar is selected from cyclohexyl and —{CH₂}ₙ—, where n=2 to 22, preferably 2 to 18 or 2 to 12, especially, 3 to 10, e.g. 3, 4, 5, 6, 8 or 10.

In all aspects of the invention, the aromatic group referred to herein as Ar is preferably phenyl/phenylene. Other aromatic moieties can be used such as naphthyl and biphenyl.

The temperature at which the reaction is conducted can be from about −50° C. to about +150° C. It is preferred to start the reaction at lower temperatures, for example at about −20° C. to about −10° C., particularly if the monomer system contains highly reactive monomers. After polymerisation has commenced, the temperature can be raised if desired, for example, to increase the rate of reaction. It is generally preferred to carry out the reaction at temperatures in the range of between about −30° C. and +25° C., particularly +20° C.

The process of the present disclosure can be carried out at relatively low temperatures, which renders the present disclosure particularly useful for the production of block copolymers. Two (or more) types of monomer can be added sequentially by opening the reactor to add the second component once the first component has reacted. Typically the nucleophilic production of PEEK requires a reaction temperature of about 350° C. Opening the reactor to add secondary monomers is problematic at this high temperature (e.g. for safety reasons). The low temperature processes of the present disclosure solve this problem. Having calculated the monomer ratios for the block length required (e.g. for a PEKK block if making a PEKXKEKK-PEKK block copolymer, the EKKE monomer to KK monomer ratio), the first monomer system is polymerised (in the presence of the Lewis acid and the controlling agent). After a suitable polymerisation time, which, using the processes of the present disclosure can be carried out at +20° C., the other monomers can be added (following optional cooling to e.g. +5° C.). Addition of further monomers is ideally carried out gradually so as to prevent the reaction temperature rising excessively.

The use of a controlling agent in the above process for preparing polymers and copolymers is preferred as it allows a stable reaction product to be achieved in a controlled and reliable manner, thus enabling production on a commercial scale. Preferably, the controlling agent is (i) a Lewis base (e.g. an aprotic Lewis base) or (ii) an aromatic carboxylic acid, aromatic sulphonic acid or a derivative thereof.

Each aromatic moiety (Ar) disclosed herein, e.g. in the polymer or in the compound Ar—O—Ar—C(=O)—X—C(=O)—Ar—O—Ar (EKXKE), may be independently selected from substituted and unsubstituted mononuclear aromatic moieties (e.g. phenyl or phenylene) and substituted and unsubstituted polynuclear aromatic moieties such as naphthyl. The term "polynuclear" is considered to encompass fused aromatic rings such as naphthalene and non-fused rings such as biphenyl, etc. Particularly preferably, Ar is phenylene or phenyl, with phenylene groups being preferably 1,4 or 1,3 phenylene (especially unsubstituted).

The phenyl, phenylene and polynuclear aromatic moieties (i.e. "Ar") may contain substituents on the aromatic rings. Such substituents would be readily understood by the skilled person and should not inhibit or otherwise interfere with the polymerisation reaction to any significant extent. Typical substituents may include, for example, phenyl, halogen (e.g. F, Cl, Br, I), ester (especially aromatic ester), nitro, carboxylic, sulphonic or phosphonic acid and the like. Preferably, the substituent should not partake in the polymerisation reaction.

In cases where X or Ar are substituted, the substituents are preferably pendant to the chains, rather than in the backbone, i.e. not bonded to a carbonyl carbon of a ketone linkage nor (in the case of Ar) to an oxygen of an ether linkage. Thus, in a particularly preferred aspect, the ketone linkages (i.e. the carbon atoms of the carbonyl group) are directly attached to carbon atoms, especially to carbon atoms of adjacent aromatic (i.e. to aromatic carbons) and/or aliphatic groups (i.e. to aliphatic carbons). Similarly, the oxygen atoms of the ether linkages are preferably attached to carbon atoms, especially to aromatic carbon atoms of adjacent aromatic groups.

Linear polymers are preferred, however cross-linked or branched polymers are also encompassed. Cross-linked or branched polymers may be produced by using cross-linking or branching agents and/or suitable monomers containing more than two suitable nucleophiles and or electrophiles. These may comprise 3, 4, 5 or 6 active groups in the methods of the present disclosure. Examples of such monomers and agents include benzene-1,3,5-tricarbonyl chloride, 1,3,5-triphenoxy benzene, benzene-2,3,5,6-tetracarbonyl chloride, benzene-1,2,3,4,5,6-hexacarbonyl chloride, 1,2,3,4,5,6-hexaphenoxy benzene, naphthalene-1,4,5,8-tetracarbonyl chloride, triphenoxybenzene, benzenetricarboxylic acid chloride, hexaphenyl benzene, $AB_2$ or $BA_2$ type moieties (such as those shown in table 5). These monomers or agents are typically used in relatively low concentrations, e.g. from 0.5M % to 25M % or between 0.5M % and 25M %.

The polymerisation process of the invention takes place in the presence of, at least, both one nucleophile (especially a dinucleophile) and one electrophile (especially a dielectrophile) and, optionally, a multi-functionalised nucleophile or electrophile if a crosslinked or branched product is required. Thus, a compound of formula Ar—O—Ar—C(=O)—X—C(=O)—Ar—O—Ar (EKXKE; the dinucleophile) and, preferably at least one other monomer, especially a dicarboxylic acid halide compound (the dielectrophile) is present. Where two different dinucleophiles (e.g. an EKXKE and ESE) make up the nucleophile components, or two different dielectrophiles (e.g. TPC and NDAC) make up the electrophile components, the polymerisation reaction of the invention can be viewed as a copolymerisation producing copolymers comprising —Ar—O—Ar—C(=O)—X—C(=O)—Ar—O—Ar—C(=O)—Ar—C(=O)— repeat units and, by way of example, —Ar—O—Ar—S(=O)$_2$—Ar—O—Ar—C(=O)—Ar—C(=O)— units for a sulphone copolymer. Thus, by "copolymer" is meant polymers comprising the aliphatic PEK moieties as herein described and one or more other units.

These other units may be selected from the following and combinations thereof:
i) aryletherketone units i.e. any EK-containing unit including other —Ar—O—Ar—C(=O)—X—C(=O)—Ar—O—Ar— units (i.e. where the —X— moieties or Ar moieties are different) or other fully aromatic EK units e.g. —{CH$_2$}$_6$— and —{CH$_2$}$_{12}$—) or EKKE
ii) non-aryletherketone units such as ether-sulphone, ether-imide, ether-amide or the like, or
iii) non-ether containing units that are suitably activated to participate in polymerisation reactions, such as bibenzyl.

References to polymers comprising a particular unit (e.g. an aliphaticaryletherketone unit and optionally also an imide unit and/or a sulphone unit) as herein described should be understood to encompass polymers containing one or more of said units or combination of units, as well as polymers consisting of, or consisting essentially of, said units or combination of units.

Suitable monomers ("comonomers") for the preparation of such copolymers are discussed herein.

Thus, viewed from a further aspect, the present disclosure provides a process for producing a copolymer (e.g. a random or block PAAEK copolymer), said process comprising:
polymerising a monomer system comprising a compound of formula: Ar—O—Ar—C(=O)—X—C(=O)—Ar—O—Ar and a comonomer (e.g. a nucleophile comonomer) in a reaction medium comprising a Lewis acid
where:
X is an aliphatic moiety and
Ar is an aromatic moiety.

Multifunctional nucleophilic and electrophilic monomers, mixtures of each type or monomers comprising both functional types may also be included.

The different combinations of nucleophile and electrophile monomers may be polymerised together (i.e. simultaneously in the same vessel) or apart (i.e. in different vessels and/or subsequent to one another). The former approach is especially suitable for the formation of random copolymers, the latter for block copolymers.

The copolymers produced may be random or block copolymers depending on their arrangement of units. Block copolymers of the present disclosure are considered to be those comprising average blocks of repeating units of at least 2, preferably 2 to 20, especially 3 to 10, e.g. at least 4 repeating units of —Ar—O—Ar—C(=O)—X—C(=O)—Ar—O—Ar—C(=O)—Ar—C(=O)— (-EKXKEKK-)$_4$ units and/or at least 2, preferably 2 to 20, especially 3 to 10, e.g. at least 4 other repeat units per block.

In all aspects of the present disclosure described herein, block copolymers (especially semi-crystalline block copolymers) are particularly preferred due to their effects on the $T_g$ and $T_m$ values compared to those of random copolymers. It is typically believed that the $T_g$ of a polymer is an attribute of the amorphous region of the said polymer, and that the crystalline state of the polymer is not a major contributor to $T_g$. Therefore, a single $T_g$ is typically quoted, irrespective of the crystalline state of a polymer. However, unexpectedly the difference in the amorphous and crystalline $T_g$ of some of the block copolymers in the present disclosure can be 20 to 30° C. Certain PAAEK block copolymers are hitherto unknown and thus form a further aspect of the present disclosure.

Random copolymers, amorphous and semi-crystalline, are generally made by the mixing of all monomers and polymerising them simultaneously.

For the formation of block copolymers, each monomer species is polymerised separately, e.g. in sequence in the same vessel or at different times and/or in different vessels and subsequently combined. For example, at least one monomer species is added after at least one other has polymerised, e.g. the dinucleophile monomer of formula Ar—O—Ar—C(=O)—X—C(=O)—Ar—O—Ar (EKXKE) is polymerised (e.g. with TPC) before or after the second (e.g. ESE), or third, dinucleophile comonomer (e.g. with TPC) or vice versa. Alternatively, in an embodiment especially suited to the formation of block copolymers, the monomers (i.e. (i) and (ii)) are polymerised in different vessels and then combined to form the copolymers of the present disclosure.

Thus, the compound of formula Ar—O—Ar—C(=O)—X—C(=O)—Ar—O—Ar (EKXKE) is preferably polymerised separately to (e.g. at a different time to or in a separate vessel from) the comonomer.

Thus, in a preferred aspect, the compound of formula Ar—O—Ar—C(=O)—X—C(=O)—Ar—O—Ar (EKXKE) is polymerised before the comonomer (e.g. ESE) is added to the reaction medium, or the comonomer is polymerised before the compound of formula Ar—O—Ar—C(=O)—X—C(=O)—Ar—O—Ar (EKXKE) is added to the reaction medium. In a further aspect, the monomers are polymerised in different vessels prior to mixing to form the copolymers of the present disclosure.

Preferably, the nucleophile monomers and comonomers will contain ether groups to activate the para carbons to electrophilic attack, while the electrophile monomers and comonomers will typically comprise carboxylic acid halides or the like. Examples of such nucleophilic comonomers, in all aspects of the present disclosure described herein, are those comprising ester, imide, sulphone and/or amide groups, preferably comprising ester, sulphone and/or amide groups, especially comprising ester and/or sulphone groups that are activated to electrophilic attack, e.g. by terminal phenoxy groups.

Where present, aryletherketone units of the copolymers of the present disclosure, in all aspects of the present disclosure described herein, include, but are not limited to the following (and combinations thereof):

Ether ketone units, i.e. EK, a unit consisting essentially of: —Ar—O—Ar—C(=O)—.

Ether ketone ketone units, i.e. EKK, a unit consisting essentially of: —Ar—O—Ar—C(=O)—Ar—C(=O)— (these are particularly preferred).

Ether ether ketone units, i.e. EEK, a unit consisting essentially of: —Ar—O—Ar—O—Ar—C(=O)—.

Ether ether ketone ketone units, i.e. EEKK, a unit consisting essentially of: —Ar—O—Ar—O—Ar—C(=O)—Ar—C(=O)—.

Ether ketone ether ketone ketone, i.e. EKEKK, a unit consisting essentially of: —Ar—O—Ar—C(=O)—Ar—O—Ar—C(=O)—Ar—C(=O)—.

These are in addition to the repeat unit of formula EKXKEKK, i.e. —Ar—O—Ar—C(=O)—X—C(=O)—Ar—O—Ar—C(=O)—Ar—C(=O)— wherein Ar is as previously described.

The copolymers, random and block, of the present disclosure may comprise one or more types of arylaliphatice-therketone repeat unit(s), e.g. derived from one or more EKXKE monomers such as $EKX_1KE$ and $EKX_2KE$ where —$X_1$— and —$X_2$— are different. Such a polymerisation results in a copolymer comprising repeating units of formula —Ar—O—Ar—C(=O)—$X_1$—C(=O)—Ar—O—Ar—C(=O)—Ar—C(=O)— and —Ar—O—Ar—C(=O)—$X_2$—C(=O)—Ar—O—Ar—C(=O)—Ar—C(=O)—. For example, where $X_1$=—$\{CH_2\}_4$— and $X_2$=—$\{CH_2\}_8$— the copolymer repeat units will be: —Ar—O—Ar—C(=O)—$(CH_2)_4$—C(=O)—Ar—O—Ar—C(=O)—Ar—C(=O)— and —Ar—O—Ar—C(=O)—$(CH_2)_8$—C(=O)—Ar—O—Ar—C(=O)—Ar—C(=O)—. Such a copolymer may be defined as PEK4KEKK-PEK8KEKK.

Where present, the aryletherketone units of the copolymers of the present disclosure may comprise one or more EK, EKK, EEK, EEKK and EKEKK units and/or other unit (non-aryletherketone units), especially those containing groups selected from ester, imide, sulphone and/or amide groups.

The method of the present disclosure allows for copolymers, random and block, including any combination of the monomers herein described, to be produced, e.g. a copolymer comprising several types of monomer such as an EKXKE-imide-ester-amide-sulphone copolymer. Particularly preferred copolymers are those comprising the following combinations of nucleophile comonomers (in combination with one or more -EKXKE- units as herein described) where for example:

$EKX_1KE$ is combined with $EKX_2KE$ (where —$X_1$— is different to —$X_2$—) and the EKXKE moieties (nucleophiles) are combined with any suitable nucleophile sulphone, imide, amine or aromatic ester monomer in the presence of suitable electrophiles. Such combinations may include EKXKE with any combination of amide, imide, sulphone or aromatic ester.

Optionally the polymers and copolymers of all types maybe end capped with a reagent which renders the chain end unreactive. Typical end capping reagents include benzoyl chloride, substituted benzoyl chlorides, 4-phenoxybenzophenone, substituted phenoxybenzophenones or other non-reactive reagents. Preferably the polymers should be end-capped with either a phenoxy or benzoyl group, especially preferred is a benzoyl group. End capping serves to control the molecular weight of any polymer or copolymer and to enhance the stability of the said polymer or copolymer.

As noted previously, the present disclosure enables the production of polymers and copolymers with a variety of useful properties. Yet further functionality can be added by incorporating amine groups into the polymers. Amine (—$NH_2$) functionalised PAAEK polymers and copolymers can be produced using a process in which the reactive amine end-capper or in-chain monomer is protected during the reaction and subsequently de-protected during the final work-up. The invention thus conveniently enables the addition of amine groups when performing the polymerisation reaction, i.e., no additional steps are required on order to achieve amine functionalisation. The use of protecting groups is common in pharmaceutical organic chemistry, but is considered novel in polymer chemistry due to the additional cost and complexity it can add to a process.

Amine-functionalised PAAEK polymers and copolymers thus form a preferred aspect of all embodiments of the present disclosure as herein described.

Viewed from a further aspect, the present disclosure provides a process for producing an amine functionalised polymer (e.g. terminated with an amine group and/or having an amine group pendant to the chain). The process comprises polymerising a monomer system comprising a compound of formula Ar—O—Ar—C(=O)—X—C(=O)—Ar—O—Ar (EKXKE; the dinucleophile) in a reaction medium preferably also including a suitable electrophile (e.g. dielectrophile) in the presence of:
(a) a Lewis acid
(b) a capping agent comprising —NR$_2$, —NRH or a protected amine group and (optionally)
(c) a controlling/dispersing agent,
where X and Ar are as herein described.

"R" is either an aliphatic or aromatic group and is defined below.

As this conveniently enables the addition of amine groups when performing the polymerisation reaction, the method is preferably a single-step reaction, i.e., no additional steps before or after polymerisation are required in order to achieve amine functionalisation.

The term "functionalised" is intended to encompass polymers and copolymers with one or more amine functional groups as end-groups or pendant groups. For linear polymers this would be up to 2 capped polymer ends and for branched polymers this could be more than 2 as branched polymers have a multiplicity of ends. It also encompasses polymers in which the amine groups are substituents pendant to the polymer chain, i.e. pendant to the backbone. Preferably, the polymers are functionalised at the chain, or branch, ends.

The polymers of the present disclosure may be "functionalised" insofar as they comprise one or more amine groups as end groups, i.e. at one or more ends of the polymer chain and/or as pendant groups, i.e. at one or more positions along the polymer backbone. With regard to particulate polymers of the present disclosure, the term "functionalised" is therefore intended to encompass amine groups on the isolated particles, at least some of which have the potential to bond with other materials, e.g. other monomers in formulations e.g. epoxides.

The preferred functional groups for the polymers of the present disclosure are amines, i.e. —NR$_2$, NRH or —NH$_2$, preferably NRH or —NH$_2$ especially —NH$_2$, and derivatives thereof, where "R" is either an aliphatic or aromatic group. Where R is an aromatic group, it is preferably Ar as herein described (especially phenyl or phenylene provided the moiety does not participate in the polymerisation). Where R of —NR$_2$ or NRH is an aliphatic group, it is preferably selected from alkyl groups, e.g. C$_1$ to C$_6$ aliphatic groups, especially methyl or ethyl groups. The compounds described herein in which the functional group is protected, i.e. those functionalised by protected amine groups as described herein, form a further aspect of the present disclosure.

Multiple amine functionalisation is also encompassed, e.g. where a phenyl ring at the end of the polymer has more than one, i.e. 1 to 5, amine groups thereon, for example 3,5-diaminodiphenylether, or where a phenyl ring in the polymer chain has more than one, i.e. 1 to 4, amine groups thereon.

Preferably, the polymers of the present disclosure are terminated with a protected amine group, i.e. a protected amine group is found on at least one end of the polymer chain that is deprotected during the work-up procedure. Typically at least 50% of the end groups are amine functionalised, i.e. the ends of the polymer chains are amine-functionalised, preferably at least 70%, especially preferably at least 85%, e.g. at least 95%. Preferably, substantially all chain ends comprise an amine group. Amine-terminated polymers are particularly preferred.

In a further aspect, as an alternative to or in addition to amine-termination of the chain, the amine groups (or protected analogues thereof) may be pendant to the polymer chain, i.e. they are substituents on the polymer's aromatic moieties. Typically, 0.1% to 100% of the Ar groups, preferably 25 to 75%, i.e. around 50% of the Ar groups have amine substitution.

The amine groups or protected amine groups may be situated on aryl groups which themselves are attached to ketone and/or ether linkages of the polymer. There may be a linker group between the aryl group of the polymer chain and the amine group. The amine groups may also be attached to an aliphatic group that is itself attached to an aromatic moiety which reacts as part of the polymerisation or end-capping process. For example, protected versions of H$_2$N—{CH$_2$}$_n$-Ph or H$_2$N—{CH$_2$}$_n$-Ph-C(=O)—Cl where the protecting group is removed as part of the standard work-up process.

In all cases, the protected amine groups are capable of being deprotected during the normal work-up procedure.

If desired, the polymers of the present disclosure may be blended with one another or with other types of polymer to form polymer blends.

Especially preferably, the compounds of the present disclosure are linear and terminated with a functional group.

Oligomeric analogues of the polymers of the present disclosure form a further aspect of the present disclosure. The processes herein described are also applicable to oligomers. As previously mentioned, a higher out of balance ratio is used to produce oligomers than is used to produce polymers. Thus, viewed from a further aspect, the present disclosure provides oligomer derivatives of the polyarylaliphaticetherketone polymers and copolymers herein described, and processes for their production, e.g. oligomers comprising one or more —Ar—O—Ar—C(=O)—X—C(=O)—Ar—O—Ar—C(=O)—Ar—C(=O)— units as herein described and optionally one or more other units as herein described. Where more than one arylaliphatic-etherketone unit is present, the compound may be monofunctional, bifunctional, trifunctional or multifunctional.

Particularly preferred oligomer compounds are those according to the following formulae:

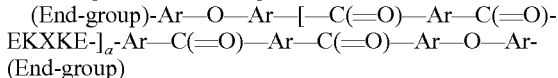

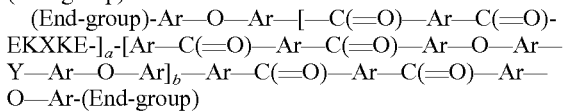

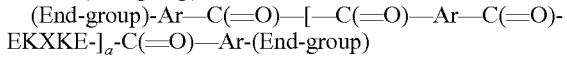

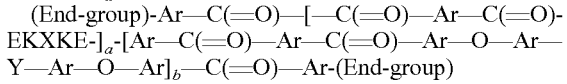

Where, Ar is an aromatic group, X is an aliphatic group as herein described, a and b are integers from 1 to 20, e.g. 1 to 10, especially 1 to 5, particularly preferably 2 to 4. Y is optionally present and may be another aromatic ether-ketone moiety, other than EKXKE, or a non-ether-ketone moiety such as sulphone or imide. The end groups may be independently selected from an amine functional group or protected amine as herein described, especially —NH$_2$ and any typical end groups for polyaryletherketone polymers, e.g. H, F, Cl, Br or I The functionalised compounds of the present disclosure are produced using a process which involves use of a protected capping agent. The capping agent comprises —NR$_2$, —NRH or a protected version of the amine group which is intended to functionalise the copolymer, monomer or oligomer. The capping agent comprises a protected amine group.

Without wishing to be bound by theory, it is thought that, if not protected, then any amine groups (especially those comprising —NH$_2$) present would react with any carboxylic acid chloride monomers to give an amide linkage in the polymer chain that is unstable compared to a ketone group. The functional capping agents therefore comprise, e.g. include, —NR$_2$, —NRH or protected amine functional groups (preferably protected amine groups), the protecting group functioning to protect the eventual amine groups during polymerisation. Capping agents comprising leaving groups (e.g. those comprising protected amine groups) are especially preferred. Capping agents comprising hydroxyl groups (—OH) are less preferred.

Especially suitable capping agents of the present disclosure are of general formula (Z)$_a$—Ar-(D)$_b$ wherein:
- each D is independently selected from —O—Ar, —C(=O)Cl, —C(=O)—Ar—O—Ar and —O—Ar—[—C(=O)—Ar—O—Ar—]$_c$-H where each Ar is independently as defined herein;
- c is an integer, e.g. 1 to 10, preferably 1 to 4,
- Z is —NR$_2$, —NRH or a protected amine group, e.g. each Z is independently selected from —NR$_2$, —NRH, —NHL, —NRL or —NL$_2$ (preferably —NHL) and L is a leaving group, such as an acetyl, haloacetyl (e.g. trifluoroacetyl), carbonate (e.g. t-Boc), sulphonyl, halosulphonyl, —SO$_2$—R, e.g. —SO$_2$—CH$_3$—SO$_2$—CF$_3$ etc. (carbonate groups such as t-Boc are less preferred);
- each R group is independently as defined herein, i.e. an aliphatic or aromatic group;
- a is 1 to 5, preferably 1, 2 or 3, especially 1 and
- b is 1 to 5, preferably 1, 2 or 3, especially 1.

Thus an example of (Z)$_a$—Ar-(D)$_b$ is CH$_3$—C(=O)—NH-Ph-O-Ph

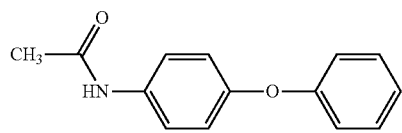

where:
Z=CH$_3$—C(=O)—NH— and a=1
Ar=phenylene
D=—O-Ph and b=1
Examples of suitable Z protected amines of the type (Z)$_a$—Ar-(D)$_b$ are:
CH$_3$—C(=O)—NH— and (CH$_3$—C(=O))$_2$—N—
CCl$_3$—C(=O)—NH— and (CCl$_3$—C(=O))$_2$—N—
CHCl$_2$—C(=O)—NH—
CF$_3$—C(=O)—NH—
CH$_3$—S(=O)$_2$—NH—
CF$_3$—S(=O)$_2$—NH—
CH$_3$-Ph-S(=O)$_2$—NH—
Etc.

In one embodiment, where Z is NL$_2$, the two leaving groups can be linked to form an imide, e.g. Z is of the following structure:

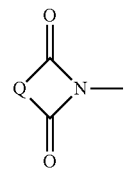

Where Q is a linker group, especially an aryl group (especially phenyl), —(CH$_2$)$_n$— or —(CF$_2$)$_n$—, where n is an integer, preferably 2 to 6. A preferred capping agent of this type is the following, which is available from Molport.

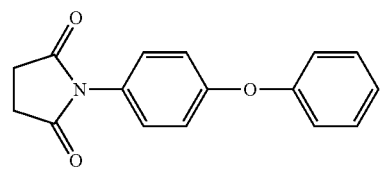

Where R is an aromatic group in —NR$_2$, —N—RH or —NRL then it must not participate in the polymerisation reaction, it is preferably Ar as herein described (especially phenyl). Where R is an aliphatic group, it is preferably selected from alkyl groups, e.g. C$_1$ to C$_6$ aliphatic groups, especially methyl or ethyl groups.

In the case where the capping agent comprises —NR$_2$ or —NRH, each R group is independently as defined herein, i.e. R is independently selected from an aliphatic or aromatic (e.g. Ph) group, preferably aliphatic, e. g. alkyl groups, e.g. C$_1$ to C$_6$ aliphatic groups, especially methyl or ethyl groups.

Preferably, the functionalised capping agent is of formula Z-Ph-O-Ph.

Particularly preferably, Z is an acetyl or haloacetyl protected amine group, e.g. —NHR especially, a trifluoroacetamide group. Especially preferred is haloacetyl.

Preferred capping agents include the following compound and its acetyl equivalent, i.e. compounds of the above formula where n is 1, Ar is Ph and R is acetyl or trifluoroacetyl:

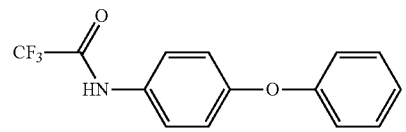

Referred to as CF$_3$-EC or 2,2,2-trifluoro-N-(4-phenoxyphenyl)acetamide

The trifluoroacetyl group has been found to be particularly straightforward to remove during the acid/base workup.

Other preferred capping agents include H$_3$C—C(=O)N(H)PhC(=O)Cl,

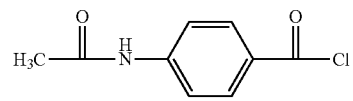

protected 3,5-diaminodiphenylether and derivatives thereof.

The protected capping agents of the present disclosure can be prepared from readily available materials such as aminobenzoic acid, diaminobenzoic acid and aminodiphenylether.

While the functional groups of the present disclosure are preferably present at the chain ends of the polymers, copolymers or oligomers, functionality pendant to the chain is also an aspect of the present disclosure. In this case, rather than a capping agent (which adds functionality or non-functionality to the end of the chains) a functionalised monomer is used. The amine functional group of the monomer must be protected in order to avoid unwanted side reactions during the polymerisation process. Suitable electrophile monomers are iso- or tere-phthalic acid chlorides comprising protected amine groups as described above. For example, the amine group of 5-aminoisophthalic acid may be protected prior to conversion of the molecule to the acid chloride.

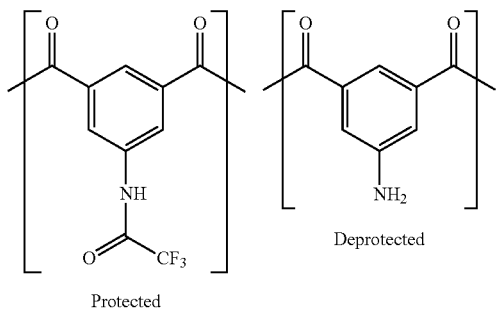

Protected    Deprotected

This can then be used in place of some of the terephthaloyl or isophthaloyl chloride monomers when preparing the PAAEK polymers and copolymers of the present disclosure.

An advantageous feature of the processes of the present disclosure is that the leaving group of the capping agent (i.e. L) is removed during standard work-up procedures following the polymerisation. There is thus no need for a separate "deprotection" step.

Typical work-up conditions which result in removal of the leaving group are the use of water, or acidic/basic aqueous solutions, e.g. solutions of HCl or NaOH. The water or solution is typically at a temperature of 0 to 100° C. at atmospheric pressure, preferably 20 to 100° C., e.g. 50 to 80° C. In some aspects, work-up can take place under pressurised conditions, e.g. at pressures of 200 kPa.

A preferred aspect of all process of the invention is that which includes a controlling/dispersing agent in the reaction medium. Suitable controlling agents include Lewis bases. The term "Lewis base" refers to a substance capable of donating an unshared electron pair to a Lewis acid. Mixtures of two or more Lewis bases can be used if desired. When a Lewis base is employed as a controlling agent, the polymer formed is typically a gel (hence the process using a Lewis base may be referred to herein as the "gel process").

Typical Lewis bases which can be employed include amides, tertiary amines, esters, ethers, ketones, nitriles, nitro compounds, phosphines, phosphine oxides, phosphoramides, sulphides, sulphones, sulphonamides, sulphoxides and halide salts. More specifically, the Lewis base may be selected from acetone, benzophenone, cyclohexanone, methyl acetate, ethylene carbonate, N-methylformamide, acetamide, N,N-dimethylacetamide, N-methylpyrrolidone, urea, tetramethylurea, N-acetylmorpholine, dimethyl sulphoxide, N,N-dimethylformamide, diphenyl sulphone, N,N-dimethylmethanesulphonamide, phosphoryl chloride, phenylphosphonyl chloride, pyridine-N-oxide, triphenylphosphine oxide, trioctylphosphine oxide, nitropropane, nitrobenzene, benzonitrile, n-butyronitrile, methyl ether, tetrahydrofuran, dimethyl sulphide, trimethylamine, N,N,N',N'-tetramethylethylenediamine, N,N-dimethyldodecylamine, imidazole, pyridine, quinoline, isoquinoline, benzimidazole, 2,2'-bipyridine, o-phenanthroline, 4-dimethylaminopyridine etc. In addition to covalent organic compounds, suitable Lewis bases include inorganic salts which can form complexes with Lewis acids, for example, chlorides, such as trimethylammonium chloride, tetramethylammonium chloride, sodium chloride or lithium chloride, perchlorates, trifluoromethanesulfonates etc.

Particularly preferred Lewis bases are dimethylsulphone, N-methylformamide, N,N-dimethylformamide, N,N-dimethylacetamide, 1-methyl-2-pyrrolidone, tetramethylene sulphone (also known as sulpholane), n-butyronitrile, dimethyl sulfide, imidazole, acetone, benzophenone, trimethylamine, trimethylamine hydrochloride, tetramethylammonium chloride, pyridine-N-oxide, 1-ethylpyridinium chloride, lithium chloride, lithium bromide, sodium chloride, sodium bromide, potassium chloride, potassium bromide and mixtures thereof.

In an alternative aspect, the controlling agent comprises an aromatic carboxylic acid, an aromatic sulphonic acid or derivatives thereof (processes using this type of controlling agent may be referred to herein as the "dispersion process"). Such acids may comprise 1, 2 or 3 carboxylic or sulphonic acid groups on an aromatic ring (i.e. these may be mono-, di- or tri-acids). Derivatives of such acids include metals salts and esters.

Preferred controlling agents for use in the method of the present disclosure include the following:
(i) $Ar(COOG)_y$;
(ii) $Ar(SO_3G)_y$;
(iii) $(ArCOO^-)_z(Met)^{z+}$; or
(iv) $(ArSO_3^-)_z(Met)^{z+}$ wherein Ar is an aromatic group compatible with the remaining components of the reaction medium;
each G independently is a hydrogen atom or an organic group (R);
each y independently is 1, 2 or 3;
each (Met) independently is a metal ion and
each z independently is an integer equal to the charge on the metal ion $(Met)^{z+}$.

The aromatic group of the controlling agent (i.e. Ar") may be selected from substituted and unsubstituted mononuclear (e.g. phenyl) and substituted and unsubstituted polynuclear aromatic moieties. Preferably the aromatic group of the controlling agent is an optionally substituted phenyl group. Preferred substituents may include halogen (e.g. F, Cl, Br, I), nitro, cyano, alkyl (e.g. $C_{1-6}$ alkyl) and the like. Alkyl substituents are preferred, e.g. methyl, ethyl, etc. Where substituents are present, these are preferably electron-withdrawing groups which deactivate the ring to electrophilic attack.

When G=R, the organic group R is preferably a straight-chained or branched $C_{1-6}$ alkyl group, i.e. the controlling agent is an alkyl ester of an aromatic carboxylic acid or aromatic sulphonic acid. More preferably, R is $C_{1-4}$ alkyl e.g. methyl.

Especially preferred controlling agents for use in the present disclosure include benzoic acid, chlorobenzoic acid (e.g. 4-chloro benzoic acid), methyl benzoic acid (e.g. 4-methyl benzoic acid), sodium benzoate, magnesium benzoate, aluminium benzoate, methyl benzoate and benzene sulphonic acid. Particularly preferably, the controlling agent is benzoic acid.

Mixtures of two or more controlling agents may also be used, if desired.

The amount of controlling/dispersing agent present is preferably from 0.1 to 6 equivalents, preferably from 0.25 to 4, especially 1 to 2 equivalents, per equivalent of acid halide groups present in the monomer system. Typical ranges of the ratio of moles of controlling agent to the moles of acid halide groups present in the monomer system are from 0.1 to 10, preferably 0.5 to 7, especially 0.7 to 5, particularly preferably 1.5 to 2. Amounts greater than 5 equivalents could be employed, if desired, e.g. up to 10 equivalents, e.g. 7 equivalents. However, no additional controlling or dispersing effect is usually achieved by adding larger amounts and it also means that more Lewis acid would be required. Thus, it is preferred to use no more than 5 equivalents, more preferably from 0.5 to 4 equivalents and especially 1 to 3 or 0.5 to 2 or 2 to 4 (e.g. 2 to 3) equivalents per equivalent of acid halide groups. A particularly preferred amount of controlling or dispersing agent is 2 equivalents per equivalent of acid halide groups.

The actual amount of controlling/dispersing agent added depends upon, inter alia, the particular controlling agent used, the nature of the monomers present, the type and amount of Lewis acid employed and the diluent. The ranges given particularly apply to the controlling agents containing one acid or base acid functionality, e.g. those listed as (i) to (iv) above where y or z is equal to 1. For those controlling agents containing more than one acid or base group per molecule, e.g. where y or z is not 1, the equivalents of controlling agent to acid halide groups in the monomer systems may be adjusted accordingly.

Many of the prior art polymerisation processes which employ controlling agents are unreliable to the extent that it cannot be predicted whether a complexed polymer in the form of a gel or a dispersion will result. Mixed solvent systems have been used in order to promote dispersion over gel formation. Whilst such systems may be used, in the methods herein described, this is not essential to achieve the desired effects. The present process therefore allows the use of a single solvent (e.g. dichloromethane) which makes solvent removal easier; the dispersion of droplets is easier to control, e.g. benzoic acid can give dispersions of the polymer in pure dichloromethane without the need for further diluents such as cyclohexane. The fact that solvent mixtures are not required makes solvent removal easier (e.g. dichloromethane can be distilled off at 41° C. with extremely high recovery rates). Use of a single solvent in the processes of the present disclosure is therefore preferred.

Moreover, controlling agents such as benzoic acid can also be readily recovered for future use when carrying out the methods of the present disclosure. The recovery of the benzoic acid controlling agent is facilitated by the fact that the acid has very low solubility in cold water but high solubility in hot water. Thus, after heating the polymer slurry in water after decomplexation, the polymer can be recovered by filtration and, on allowing the filtrate to cool, the benzoic acid crystallises out facilitating its recovery for future use. An alternative method to recover the benzoic acid would be to add sufficient sodium hydroxide to form water soluble sodium benzoate (1 g in 2 mL of water). On filtration and isolation of the polymer, an acid such as hydrochloric acid can be added to the filtrate to reform the benzoic acid which would precipitate from the filtrate.

The ability to recover the solvent and the controlling agent together with the reduction in the amount of water required in the process provides a more sustainable and cost-effective process than the prior art methods which require solvent mixtures, controlling agents which are difficult to remove and large quantities of water.

If necessary, capping agents which do not contain an amine group (protected or otherwise) may be added to the polymerisation reaction medium to cap the polymer or copolymer on at least one end of the polymer chain. This terminates continued growth of that chain and controls the resulting molecular weight of the polymer. Use of these capping agents may therefore be used to produce polymers or copolymers within a selected narrow molecular weight range. In this aspect, both nucleophile and electrophile capping agents may be used to cap the polymer or copolymer at each end of the chain or branch. Such non-functionalised capping agents may be used in addition to, or as an alternative to, the functionalised capping agent which comprises —$NR_2$, —NRH or a protected amine, which is used to produce the functionalised compounds of the present disclosure. Preferred nucleophilic capping agents of this type are 4-chlorobiphenyl, 4-phenoxybenzophenone, biphenyl, 4-phenoxydiphenylsulphone, and the like. Typical electrophilic capping agents include benzoyl chloride, benzenesulfonyl chloride and the like.

A Lewis acid is used as the catalyst for polymerisation and copolymerisation (and for the preparation of the novel EKXKE monomer). The term "Lewis acid" is used to refer to a substance which can accept a shared electron pair from another molecule. Suitable catalysts for use in the method of the present disclosure include aluminium trichloride, aluminium tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Preferably the catalyst is substantially anhydrous aluminium trichloride.

The amount of Lewis acid catalyst used will vary depending on the particular monomers and the reaction medium selected. Typically, the amount of Lewis acid required is calculated on the basis of one mole of Lewis acid for each mole of ketone or sulphone units, plus an amount equimolar to that of Lewis base, or controlling agent, plus up to 20% excess. Larger excesses can be used but offer no significant advantage.

Alternative catalyst systems for electrophilic processes include use of trifluoromethanesulphonic acid, with and without $P_2O_5$, and those using mixtures of $CF_3$—COOH and $CF_3$—$SO_3H$ with and without $P_2O_5$. Terephthalic and isophthalic acids can be used in these super acid mixtures. For example, PEKK can be produced from EKKE plus terephthalic and isophthalic acids in $CF_3$—$SO_3H$, where the $CF_3$—$SO_3H$ is used as the solvent. The $CF_3$—$SO_3H$ reacts with the terephthalic/isophthalic acids to give the mixed carboxylic-sulphonic anhydride $CF_3$—$SO_2$—O—CO-Ph-CO—O—$SO_2$—$CF_3$ which, in the presence of electron rich para-carbon moieties, as in EKKE, then eliminate $CF_3$—$SO_3H$ and forms a ketone unit. As an alternative to $CF_3$—$SO_3H$, $CF_3$—COOH with some $CF_3$—$SO_3H$, plus $P_2O_5$ to remove the condensation water produced, may be used. The condensation water being produced from the reaction of the carboxylic acid with the super acid to form the anhydride.

Preferred solvents for the electrophilic polymerisation reaction are halogenated hydrocarbons (e.g. tetrachloroethylene, 1,2,4-trichlorobenzene, o-difluorobenzene, 2-dichloroethane, dichlorobenzene, 1,1,2,2,-tetrachloroethane, particularly ortho-dichlorobenzene, dichloromethane etc.). Additionally, or alternatively, non-chlorinated diluents may be used such as cyclohexane, carbon disulphide, nitromethane, nitrobenzene, HF. Dichloromethane (DCM) is particularly preferred for use in the present disclosure.

A non-protic diluent can also be employed, if desired. The diluent should be inert towards Friedel-Crafts reactions. Diluents include, for example, dichloromethane, carbon disulphide, o-dichlorobenzene (i.e. ortho- or 1,2-dichlorobenzene), 1,2,4-trichlorobenzene, o-difluorobenzene, 1,2-dichloroethane, cyclohexanes, 1,1,2,2,-tetrachloroethane and mixtures thereof. Whilst these additional diluents may be used they confer no significant advantage to the process and may result in difficulty in separating the diluents used for further use. A process which is substantially free from co-solvent is therefore a preferred aspect of the present disclosure.

The amount of any diluent, or mixtures of diluents, used is most preferably in the range of 10 mL to 400 mL, especially 50 mL to 200 mL of diluent to 10 g of polymer. Both higher and lower concentrations (preferably higher) may be used if required.

When electrophilic polymerisation is complete, the polymer contains Lewis acid catalyst complexed to all carbonyl or sulphonyl groups (and possibly also to ether groups). The catalyst residue must be removed, i.e. the Lewis acid must be decomplexed from the polymer and removed. Decomplexation can be accomplished by treating the polymerisation reaction mixture with a decomplexing base after completion of polymerisation. The decomplexing base must be at least as basic towards the Lewis acid as the basic groups on the polymer chain.

The amount of decomplexing base used should be in excess of the total amount of bound (complexed) and unbound Lewis acid present in the reaction mixture and is preferably at least twice the total amount of Lewis acid. Typical decomplexing bases which can be used include water, dilute aqueous hydrochloric acid, methanol, ethanol, acetone, N,N-dimethylformamide, N,N-dimethylacetamide, pyridine, dimethyl ether, diethyl ether, tetrahydrofuran, trimethylamine, trimethylamine hydrochloride, dimethyl sulphide, tetramethylene sulphone, benzophenone, tetramethylammonium chloride, isopropanol, acetic acid and the like. Iced water or cooled dilute hydrochloric acid are preferred for use in the present disclosure.

The reactions are usually carried out in a dry and/or inert, preferably dry, especially dry and inert atmosphere, e.g. reaction vessels may be purged with dry air, nitrogen, argon or $CO_2$. Typically, the catalyst (e.g. $AlCl_3$) is added to the cooled solvent (preferably dichloromethane, preferably cooled to well below room temperature, e.g. −20° C.) followed by the controlling/dispersing agent (preferably benzoic acid or dimethylsulphone) followed by the monomers (electrophilic and nucleophilic) and (optional) a functionalised or non-functionalised end-capper. Further single monomer, or monomer mixtures if required, may then be added as a solution in the same solvent or as solids. The controlling agent may be added earlier or later in the sequence of additions, preferably after the catalyst and before the monomers, provided the temperature of the slurry is kept below −10° C. during the addition, preferably below −20° C. Additional reaction components, e.g. capping agents, additional diluent etc., are typically also added at this stage. If used, the capping agent can be added later, even after the mixture has warmed. This has the effect of altering the molecular weight distribution which can be advantageous in some instances and may reduce the overall reaction time. This can also be used to alter the molecular weight distribution.

This in a preferred aspect, the Lewis acid is added to the reaction medium prior to the controlling agent. In a particularly preferred aspect, the components are added to the reaction medium in the following order:
 (i) Lewis acid
 (ii) controlling agent
 (iii) monomers (and optionally capping agent).

The resulting reaction mixture is then typically allowed to warm towards room temperature while being stirred vigorously in a suitably baffled or non-baffled reactor. During the polymerisation or copolymerisation, any by-products (e.g. condensation products such as hydrogen chloride) can be trapped and disposed of. After stirring (if a dispersion) or standing (if a gel) at room temperature for a suitable length of time (in general 4 to 8 hours, preferably 6 hours), work-up/decomplexation can begin by combining the entire reaction mass with decomplexing base (e.g. iced water). Care must be taken to avoid the temperature of the decomplexing mixture rising above room temperature (+25° C.). Prior to decomplexation, the reaction mass is typically an orange slurry or gel, and after complete decomplexation the mass is usually a snow white/off white slurry. Where the polymerisation or copolymerisation forms a gel the decomplexation is undertaken using a high speed blender in the presence of ice and water at an initial temperature of 5° C. In the case of imide containing copolymers, the decomplexed mass may be yellow or pale yellow. The mass is then typically stirred at or below room temperature to yield the final polymer product as a white, off white or yellow powder, fluff or flake.

Solvent removal from this product may be carried out by any conventional method, although typically this will be by distillation. Further purification of the polymer can be achieved by known methods, e.g. hot filtration of the suspension to yield the polymer product, typically as a snow white/off white or yellow powder, fluff or flake. Where benzoic acid is used as the controlling agent, cooling of the combined filtrates, including any acidic washes (e.g. to 5° C.) results in the recovery of benzoic acid by crystallisation. When dimethylsulphone is used, it is not recoverable. Using these methods, up to 95% of the solvent, usually dichloromethane, can be recovered along with up to 90% of the controlling agent (e.g. when the controlling agent is benzoic acid or a benzoic acid derivative).

The polymers produced by way of the methods herein described are considered to form a further aspect of the present disclosure. Thus, in a further aspect, the present disclosure provides a PAAEK polymer, oligomer or copolymer obtainable by any process as herein described.

From a further aspect, the present invention provides a polymer, oligomer or copolymer comprising the repeat unit —Ar—O—Ar—C(=O)—X—C(=O)—Ar—O—Ar—C(=O)—Ar—C(=O)—, where Ar and X are as herein described, or a copolymer thereof. Preferably, the polymer or oligomer consists essentially of the repeat unit —Ar—O—Ar—C(=O)—X—C(=O)—Ar—O—Ar—C(=O)—Ar—C(=O)—.

Especially preferably, X in the compounds mentioned herein is selected from cyclohexyl and —{$CH_2$}$_n$— where n=2 to 22, preferably 2 to 18 or 2 to 12, especially, 3 to 10, e.g. 3, 4, 5, 6, 8 or 10.

The polymers, oligomers and copolymers of the invention are preferably amine functionalised, i.e. they comprise amine functional groups at the end of the chain or pendant to the chain.

A further advantage of the present disclosure is that the process comprising the use of an aromatic carboxylic/sulphonic acid controlling agent can yield the polymers of the invention in particulate form e.g. spheres/particles of the polymers. Alternatively, where a controlling agent such as dimethylsulphone is used, the polymer is isolated as either fluff or flake. The form of the isolated polymer, or copolymer, is useful in extending potential uses for the materials.

The polymers of the invention are preferably in particulate, fluff or flake form. Where the form is particulate, the particles are spherical, substantially spherical or lozenge shaped. Product arising from the "gel process", i.e. that using a Lewis base as a controlling agent, is jagged and irregular.

The particle shape may be irregular, e.g. lozenge shaped, fibrous or rod shaped, preferably with an aspect ratio (R) of 1.5 to 10 (where R=a/b, "a" is the largest dimension, and "b" is the smallest dimension), however, in preferred embodiments, the polymer particles are primarily, i.e. substantially, spherical, preferably substantially spherical in shape with an aspect ratio (R) of about 1 to 1.5. The polymer is semi-crystalline, with the degree of crystallinity greater than 5%. Semi-crystalline polymers and copolymers usually exhibit good chemical resistance and low moisture pick-up compared to amorphous polymers. In some instances the isolated polymer particles fluff or flake may be semi-crystalline as isolated but the polymer or copolymer is amorphous after melt processing. The particles' physical structure may range from being solid (high density; e.g. density of 1.3 g/cc or greater) to cellular (density of <1 g/cc) structure, or a combination of the two.

The size of the spherical polymer particles may be controlled by varying the amount of dispersant (i.e. controlling agent, such as benzoic acid) added, amount of polymer per unit volume of solvent, the stirrer speed, the stirrer paddle design, temperature ramp rate, the reactor design and/or the addition of baffles to create turbulence. Other techniques well known in dispersion polymer chemistry may be employed. However, the present inventor has surprisingly found that, not only can the present disclosure provide spherical particles of the polymers of the invention for the first time, but the method allows the particle size (e.g. distribution and/or mean) to be controlled by varying the amount of controlling agent used.

It has been found that increasing the amount of carboxylic/sulphonic acid based controlling agent relative to the amount of monomers results in the average particle size decreasing. Typical ranges of ratio of moles of controlling agent to moles of acid halide groups are described herein.

The actual amount of controlling agent added depends upon, inter alia, the particular controlling agent used, the nature of the monomers present and the type and amount of Lewis acid employed. As noted above, the ranges given particularly apply to the controlling agents containing one carboxylic acid or sulphonic acid functionality, e.g., those listed as (i) to (iv) above where y or z is equal to 1. For those controlling agents containing more than one acid group per molecule, e.g. where y or z is not 1, the equivalents of controlling agent to acid halide groups in the monomer systems may be adjusted accordingly.

The higher relative amounts of controlling agent can produce particles of a smaller mode particle size than the lower amounts of controlling agent. It has been found that controlling the particle size is particularly suited to polymers in which the 1,4-linked units are present in 50% or more by weight.

As well as decreasing the size of the particles produced, increasing the relative amount of controlling agent used can result in extremely small particles being formed. For example, particles of less than one micron, i.e. as small as 0.275 μm have been recorded. If very small particles are desired, the amount of controlling agent (and/or other factors known to influence particle size in polymerisation reactions) can be chosen to optimise the amount of smaller particles and the smallest particles removed from the product mixture, e.g. by using conventional techniques such as sieving, air classification (e.g. air elutration), photoanalysis, optical counting methods, electroresistance counting methods, sedimentation techniques, laser diffraction methods, acoustic spectroscopy, ultrasound attenuation spectroscopy etc.

Where the particles are spherical, by "particle size" is meant particle diameter. The particles according to the present disclosure advantageously have particle sizes (as measured with a Malvern Mastersizer particle size analyser) of 0.1 to 3000 μm, preferably 1 to 500 μm, especially preferably 1 to 100 μm, particularly 10 to 200 μm, e.g. 50 to 100 μm. Preferably the particles have one dimension that is 75 μm or less, e.g. 10 to 50 μm. Especially preferably, the particles are substantially spherical particles having diameter of less than 75 μm. Preferably, the particles are substantially spherical in shape with an aspect ratio (R) of about 1 to 1.5. Typically, at least 25% (by volume) of the particles are less than 100 μm in diameter, preferably at least 50%, e.g. at least 75%. Alternatively, or additionally, at least 20% of the particles are less than 70 μm, preferably at least 40%, e.g. at least 60%.

Where the particles are irregular (fluff or flake), the particles are preferably no more than 3 mm by 2 mm on average, more preferably less than 1 mm.

The provision of spherical particles directly from the polymer or copolymer production process is particularly advantageous as it means that costly further processing steps such as grinding and sieving are not necessary if powders are required. Selected sieving may be used where particle size ranges are required or simply to remove larger particles. The disclosed "dispersion" process gives spherical particles directly. Moreover, the spherical particles produced according to the present disclosure are more smooth and uniform in shape compared to the rough particulates that would be produced by grinding.

By varying the amount of controlling/dispersing agent and separating the particles based on their size, the present disclosure allows PAAEK polymers and copolymers particle size ranges to be produced. This lends the polymers and copolymer to a variety of different applications as the size range of the particles can be controlled to suit the end use. For example, very small (e.g. sub-micron particles) could be used for powder impregnation of composites. Where the controlling agent produced a polymer gel then the particles are jagged.

Thus the present disclosure provides a method for producing polymers and copolymers as herein described, having a selected particle size distribution, said method comprising the following steps:

(i) polymerising a monomer system (comprising nucleophile and electrophile moieties as herein described) in a reaction medium comprising:

(a) a Lewis acid;
(b) a controlling agent comprising an aromatic carboxylic acid, an aromatic sulphonic acid, or a derivative thereof; and (optionally)
(c) a functionalised or non-functionalised capping agent comprising a —NR$_2$, —NRH or a protected amine functional group or a non-reactive capping agent such as benzoyl chloride.

and
(ii) adjusting the ratio (e.g. molar ratio) of controlling agent to monomers in the monomer system whereby to control particle size.

The present disclosure further provides a method for producing polymers and copolymers as herein described, as fluff or flake, said method comprising the following steps:
(i) polymerising a monomer system (comprising nucleophile and electrophile moieties as herein described) in a reaction medium comprising:
(a) a Lewis acid;
(b) a controlling agent comprising a Lewis base controlling agent such as dimethylsulphone; and (optionally)
(c) a functionalised or non-functionalised capping agent comprising a —NR$_2$, —NRH or a protected amine functional group or a non-reactive capping agent such as benzoyl chloride.

and
(ii) adjusting the ratio (e.g. molar ratio) of controlling agent to monomers in the monomer system whereby to give a good polymer distribution in a gel.

Preferably, the particle size of the spherical particles is selected by adjusting the ratio of moles of benzoic acid derived controlling agent to moles of acid halide groups present in the monomer system. Typical ratios of moles of controlling agent to moles of acid halide groups present in the monomer system are as described herein, e.g. from 0.1 to 10, preferably 0.25 to 4 or 0.5 to 7, especially 0.7 to 5, particularly preferably 1 or 1.5 to 2, e.g. 2.

As noted above, the present disclosure provides, for the first time, a method for the production of block and random copolymers comprising at least partially the repeat unit —Ar—O—Ar—C(=O)—X—C(=O)—Ar—O—Ar—C(=O)—Ar—C(=O)—. Block and random copolymers of the polymers herein described therefore form a further aspect of the present disclosure.

Preferably the polymers and copolymers of the present disclosure have an inherent viscosity (IV) of at least 0.3 dl/g, e.g. at least 0.4 dl/g, especially at least 0.5 dl/g, particularly preferably at least 0.7 dl/g when measured as 0.1 weight % solutions in concentrated sulphuric acid at 25° C.

Preferably the polymers and copolymers of the present disclosure melting temperatures (T$_m$). ranging between 180° C. and 350° C., most preferably between 200° C. and 300° C., e.g. 220 to 280° C.

Preferably the polymers and copolymers of the present disclosure have glass transition temperatures (T$_g$) ranging between 50° C. and 200° C., most preferably between 70° C. and 140° C., as measured by differential scanning calorimetry (DSC).

As already noted, the polymers and copolymers of the present invention can be produced due to the applicant's surprising finding that a compound of formula Ar—O—Ar—C(=O)—X—C(=O)—Ar—O—Ar (EKXKE) can be reliably isolated. This compound is less reactive than diphenyl ether (which is a common starting material for making EK polymers and earlier attempts to produce high molecular weight PAAEKs) and therefore delivers a more stable polymer or copolymer. Thus, viewed from a further aspect, the present invention provides a compound of formula Ar—O—Ar—C(=O)—X—C(=O)—Ar—O—Ar, where X is an aliphatic moiety as herein defined and Ar is an aromatic moiety.

Especially preferably, X in the compound of formula Ar—O—Ar—C(=O)—X—C(=O)—Ar—O—Ar (EKXKE) is selected from cyclohexyl and —{CH$_2$}$_n$— where n=2 to 22, preferably 2 to 18 or 2 to 12, especially, 3 to 10, e.g. 3, 4, 5, 6, 8 or 10.

The novel compounds of formula Ar—O—Ar—C(=O)—X—C(=O)—Ar—O—Ar (EKXKE) can be prepared via a process comprising reacting diphenyl ether with a dicarboxylic acid halide of X. Thus, viewed from a further aspect, the present invention provides a process for preparing a compound of formula Ar—O—Ar—C(=O)—X—C(=O)—Ar—O—Ar (EKXKE), said process comprising reacting diphenyl ether with a dicarboxylic acid halide of X in the presence of a Lewis acid, wherein the moles of diphenyl ether are in excess with respect to the moles of the dicarboxylic acid halide of X.

Ph-O-Ph needs to be present in excess relative to the dicarboxylic acid halide of X to ensure that the desired monomeric compound of formula Ar—O—Ar—C(=O)—X—C(=O)—Ar—O—Ar (EKXKE) is prepared. It is thought that, during the reaction, once one end of the Ph-O-Ph is substituted then the electron withdrawing effect of the CO at the other end also moderately deactivates the unsubstituted end of the now mono-substituted Ph-O-Ph compared to the unsubstituted Ph-O-Ph. Preferably, the diphenyl ether to dicarboxylic acid halide molar ratio is at least 2:1, especially 3:1.

Temperature control also assists in the production of the monomeric compound. For example, suitable reaction temperatures for this process are −20° C. to +25° C.

As an alternative to dicarboxylic acid halides of X, other compounds containing the X group together with groups that would take part in a Friedel-Crafts reaction can be used. Such groups include tosyl and CF$_3$—SO$_3$— units or groups such as —OR, where R is methyl, ethyl, isopropyl or other lower alkyl.

An alternative synthetic route to the monomers EKXKE is to react the dicarboxylic acid chloride of X with excess halobenzene, e.g. fluorobenzene, under Friedel-Crafts conditions giving the product Hal-Ph-C(=O)—X—C(=O)-Ph-Hal (e.g. F-Ph-C(=O)—X—C(=O)-Ph-F) and then subsequently reacting this product with a phenate salt such as sodium or potassium phenate. Preferably, one or both stages of the reaction should be conducted in a dipolar aprotic solvent, and/or at elevated temperature. Thus, viewed from a further aspect, the present invention provides a process for preparing a compound of formula Ar—O—Ar—C(=O)—X—C(=O)—Ar—O—Ar (EKXKE), said process comprising reacting a dicarboxylic acid halide of X with excess halobenzene (e.g. fluorobenzene) in the presence of a Lewis acid to produce Hal-Ph-C(=O)—X—C(=O)-Ph-Hal (e.g. F-Ph-C(=O)—X—C(=O)-Ph-F) and subsequently reacting Hal-Ph-C(=O)—X—C(=O)-Ph-Hal with a phenate salt, e.g. sodium or potassium phenate, preferably in a dipolar aprotic solvent, preferably at elevated temperature.

In a preferred aspect the dicarboxylic acid halide used in preparation of the compound of formula Ar—O—Ar—C(=O)—X—C(=O)—Ar—O—Ar (EKXKE) is a compound of formula ClC(=O)—X—C(=O)Cl.

The compounds described herein e.g. polymers, oligomers, copolymers, functionalised polymers, block copolymers, flakes and spherical particles of polymer, form a further aspect of the present disclosure, as do their uses and articles/composites comprising them.

Compositions comprising the compounds and polymers as herein described, e.g. spherical particles of the polymers, may contain or comprise the particles (e.g. spherical particles) in a suitable matrix, for example another polymer, such as a thermoplastic or thermoset. The particles can also be utilised as the powders in powder impregnated fibre composites.

The polymer or copolymer particles may be solid, hollow or porous, e.g. porous with an outer shell. In the case where porous or hollow particles are formed, these may be used to encapsulate or support materials, e.g. active agents in order to impart extra functionality to the polymer. For example, the cellular structure of particles of the present disclosure can allow penetration of liquid thermoset resin to infuse and react to form an interpenetrating network at the particle surface.

The functional groups of the materials of the present disclosure may be used to attach the polymer (e.g. polymer particles) covalently to other materials, e.g. other polymers, and can be used, for example, in the production of toughened polymer materials.

The polymers or copolymers of the present disclosure may be blended with other polymers in order to produce polymer blends suited to a variety of purposes. Moreover, articles comprising the polymers of the present disclosure form a further aspect of the present disclosure.

The polymers and copolymers of the present disclosure are particularly useful for use in structural components, composites, additive layer manufacturing, fibres, films, electrical and medical applications.

The present disclosure will now be further described in the following non-limiting examples.

Example 1—Synthesis of PEK(10)KEKK (Gel Method): all Isophthaloyl, 2% OOB

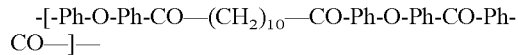

A 5 L jacketed reaction vessel fitted with an efficient stirrer, thermometer, nitrogen inlet and gas outlet, containing 1.5 L of anhydrous dichloromethane was cooled to −20° C. under a nitrogen purge. To the cold stirred dichloromethane was added 458.35 g (3.44 moles) of anhydrous aluminium trichloride. During this addition the temperature of the dichloromethane rose to −12° C. After re-cooling to −15° C., 70.5 g (0.75 moles) of dimethyl sulphone was slowly added to the slurry keeping the temperature of the slurry below −5° C. At −10° C., 101.51 g (0.5 moles) of Isophthaloyl chloride was added to the reaction mixture. Care was taken to ensure that all Isophthaloyl residues from the beaker and that caught on the addition funnel were completely washed into the reaction vessel using 100 ml of fresh dichloromethane. The temperature rise during this addition was minimal. Again at −15° C., 272.68 g (0.51 moles) of 1,10-bis(4-phenoxybenzoyl)decane (EK10KE) was slowly added to the slurry while maintaining the reaction temperature below −10° C. Residual EK10KE was carefully washed into the reaction vessel using 100 ml of fresh dichloromethane. After connecting the reaction vessel to an acid gas scrubber, the temperature of the reaction mixture was increased to +20° C. over 45 minutes. During this time all of the reaction solids dissolved to give a clear orange solution and hydrogen chloride was seen to be evolved. The temperature of the reaction vessel was maintained at +20° C. for 6 hours. During the first 1.5 hours the viscosity of the orange solution increased until a gel was formed stopping the stirrer. At this point the stirrer was switched off.

The polymer complex was decomplexed by blending the orange rubbery mass in a Waring blender in the presence of ice and water, the blending mixture being kept below +20° C. During this process the polymer turned from orange to snow white. The white polymer fluff was filtered and washed on the filter with 2×2 L of deionised water. After sucking the fluff dry it was slurried overnight in 4 L of deionised water at room temperature. After filtering the fluff was slowly added to 4 L of hot (70° C.) deionised water in portions to minimise foaming as the dichloromethane was removed. The white slurry was then refluxed for 2 hours to ensure complete removal of the dichloromethane. The fluff was then filtered again and the fluff washed on the filter with 2×2 L of deionised water. This process was then repeated. After the repeat the fluff was further refluxed for 1 hour in 4 L of deionised water containing 100 ml of 0.88 ammonia. After filtering and washing with 2×2 L of deionised water the fluff was finally again refluxed in 4 L of deionised water, filtered and washed.

The polymer fluff was dried overnight (16 hours) at 100° C. followed by a further drying at 140° C. for 8 hours under vacuum.

Optionally the polymer can be end capped using benzoyl chloride.

The above synthesis give a polymer with phenoxy end groups as the synthesis was carried out 2% out of balance.

The IV of the polymer was 1.29 gl/g measure as a 0.1% solution in concentrated sulphuric acid.

The $T_g$ of the polymer was at 76° C., $T_c$ at 153° C. and $T_m$ 197° C. measure using DSC from a fully quenched amorphous sample.

The TGA of the polymer in air showed a 1% weight loss at 330° C.

The polymer was shown to be 38% crystalline by XRD.

Melt viscosity of the polymer measured at 71 Hz at 250° C. showed the polymer to have a viscosity of 5100 Pa·s after 10 mins and 6000 Pa·s after 30 mins.

The flexural modulus of the polymer at 23° C. was 2.78 GPa.

The yield strength of the polymer was 70 MPa at 23° C., elongation to yield was 4.9% and elongation to break was 24% at 23° C.

The polymer was fully characterised by $^1$H and $^{13}$C NMR spectroscopy and found to be linear.

Example 2—Synthesis of PEK-10-KEKK all Terephthaloyl

Carried out as in example 1 using terephthaloyl chloride in place of isophthaloyl chloride 1.5% out of balance. IV=1.4 dl/g $T_g$ 74.5° C.; $T_{c1}$ 92.8° C.; $T_{c2}$ 221° C.; $T_m$ 276.5° C.

Example 3—Synthesis of PEK-10-KEKK all Terephthaloyl

As in example 2 using dimethylacetamide in place of dimethylsulphone. IV=1.22 dl/g $T_g$ 75° C.; $T_{c1}$ 93.5° C.; $T_{c2}$ 221° C.; $T_m$ 276° C.

Example 4—Synthesis of PEK-4-KEKK all Terephthaloyl

As in example 1 where the monomer EK-10-KE was replaced by the monomer EK-4-KE. Isophthaloyl chloride was replaced by terephthaloyl chloride.

IV=0.92 dl/g
$T_g$ 119° C.; $T_{c1}$ 143° C.; $T_{c2}$ 232° C.; $T_{m1}$ 305° C.; $T_{m2}$ 328° C.

Example 5—Synthesis of PEK-Cyclohexyl-KEKK all Terephthaloyl

As in example 1 where the monomer EK-10-KE was replaced by the monomer EK-cyclohexyl-KE and Isophthaloyl chloride was replaced by terephthaloyl chloride. IV=1.83 dl/g
$T_g$ 172° C.; $T_c$ 220° C.; $T_m$ 350° C.

Example 6—Synthesis of PEK-Cyclohexyl-KEKK all Isophthaloyl

As in example 5 where the terephthaloyl chloride was replaced by Isophthaloyl chloride. IV=0.87 dl/g
$T_g$ 157° C.; $T_c$ 276° C.; $T_{m1}$ 268° C.; $T_{m2}$ 303° C.

Example 7—Synthesis of PEK-3-KEKK all Terephthaloyl

As in example 1 where the monomer EK-10-KE was replaced by the monomer EK-3-KE and isophthaloyl by terephthaloyl chloride. IV=1.59 dl/g
$T_g$ 127° C.; $T_c$ 220° C.; $T_m$ 280° C.

Example 8—Synthesis of PEK-5-KEKK all Terephthaloyl

As in example 1 where the monomer EK-10-KE was replaced by the monomer EK-5-KE and isophthaloyl by terephthaloyl chloride. IV=0.88 dl/g
$T_g$ 114° C.; $T_{c1}$ 148° C.; $T_{c2}$ 236° C.; $T_m$ 285° C.

Example 9—Synthesis of PEK-8-KEKK all Terephthaloyl

As in example 1 where the monomer EK-10-KE was replaced by the monomer EK-8-KE and isophthaloyl by terephthaloyl chloride. IV=0.98 dl/g
$T_g$ 89° C.; $T_c$ 228° C.; $T_m$ 285° C.

Example 10—Synthesis of Copolymer PEK-4-KEKK-EK-10-KEKK

As in example 1 where the monomer EK-10-KE was replaced by the monomers EK-10-KE and EK-4-KE in the ratio 1:2 and isophthaloyl by terephthaloyl chloride. IV=1.01 dl/g
$T_g$ 99° C.; $T_{c1}$ 126° C.; $T_{c2}$ 229° C.; $T_m$ 298° C.

Example 11—Synthesis of PEK-8-KEKK, Isophthaloyl Terephthaloyl

As in example 1 where the monomer EK-10-KE was replaced by the monomer EK-8-KE and the monomer isophthaloyl chloride was replaced by the mixed monomers terephthaloyl and isophthaloyl chloride in the ratio 2:3. IV=0.95 dl/g
$T_g$ 83° C.; $T_{c1}$ 147° C.; $T_{m1}$ 200° C.; $T_{c2}$ 211° C.; $T_{m2}$ 230° C.

Example 12—Synthesis of PEK-6-KEKK Isophthaloyl Terephthaloyl

As in example 1 where the monomer EK-10-KE was replaced by the monomer EK-6-KE and the monomer isophthaloyl chloride was replaced by the mixed monomers terephthaloyl and isophthaloyl chloride in the ratio 2:3. IV=1.03 dl/g
$T_g$ 96° C.; $T_{c1}$ 180° C.; $T_{m1}$ 208° C.; $T_{c2}$ 211° C.; $T_{m2}$ 254° C.

Example 13—Synthesis of the Co-Polymer PEK10KEKK-PEKK

As in example 1 where the monomer EK10KE was replaced by a mixture of the monomers EK10KE and 1,4-bis(4-phenoxybenzoyl)benzene (EKKE) in the ratio 3:1. IV=1.31 dl/g.
The polymer was amorphous with a $T_g$ at 91° C.

Example 14—Synthesis of PEK8KEKK Isophthaloyl Terephthaloyl

As in example 1 where the monomer EK10KE was replaced by the monomer EK8KE and the monomer isophthaloyl chloride was replaced by the mixed monomers terephthaloyl and isophthaloyl chloride in the ratio 3:2. IV=1.00 dl/g
$T_g$ 90° C.; $T_c$ 142° C.; $T_{m1}$ 212° C.; $T_{m2}$ 255° C.

Example 15—Dispersion Synthesis of the Copolymer PEK10KEKK-PEKK

As in example 13 where the ratio of EK10KE to EKKE was 7:3, the ratio of terephthaloyl to isophthaloyl chlorides was 1:1 and where the dimethyl sulphone was replaced by benzoic acid where the ratio of benzoic acid to total terephthaloyl and isophthaloyl chlorides was 4:1. The product was isolated as a fine orange powder which was white after decomplexing. The first stage of the work up was to heat to reflux the white slurry in 10% aqueous hydrogen chloride for one hour. The same work up procedure was then followed as in example 1. IV=1.12 gl/g
$T_g$ 78° C.; $T_c$ 114° C.; $T_m$ very broad 265° C.

Example 16—Dispersion Synthesis of the Polymer PEK-10-KEKK Isophthaloyl Terephthaloyl As in example 1 where the terephthaloyl to isophthaloyl ratio was 1:1 and where the dimethyl sulphone was replaced by benzoic acid where the ratio of benzoic acid to total terephthaloyl to isophthaloyl chlorides was 1:4. The product was isolated as a fine orange powder which was white after decomplexing. The first stage of the work up was to heat to reflux the white slurry in 10% aqueous hydrogen chloride for one hour. The same work up procedure was then followed as in example 1. IV=0.82 dl/g
$T_g$ 76° C.; $T_{c1}$ 105° C.; $T_{c2}$ 212° C.; $T_m$ 255° C.

Example 17—Dispersion Synthesis of the Copolymer PEK10KEKK-PESEKK

As in example 13 where the ratio of EK10KE to 4,4'-diphenoxydiphenylsulphone (ESE) was 2:1, the acid chloride was 100% terephthaloyl chloride and where the dimethyl sulphone was replaced by benzoic acid where the ratio of benzoic acid to terephthaloyl chloride was 4:1. The product was isolated as a fine orange powder which was white after decomplexing. The first stage of the work up was to heat to reflux the white slurry in 10% aqueous hydrogen chloride for one hour. The same work up procedure was then followed as in example 1. IV=0.74 gl/g
$T_g$ 100° C.; $T_{c1}$ 152° C.; $T_{c2}$ 207° C.; $T_m$ 249° C.

Example 18—Dispersion Synthesis of the Copolymer PEK10KEKK-PEIEIEKK

As in example 13 where the ratio of EK10KE to imide monomer (EIEIE) was 4:1, the acid chloride was 100% terephthaloyl chloride and where the dimethyl sulphone was replaced by benzoic acid where the ratio of benzoic acid to terephthaloyl chloride was 4:1. The product was isolated as a fine orange/red powder which was white after decomplexing. The first stage of the work up was to heat to reflux the white slurry in 10% aqueous hydrogen chloride for one hour. The same work up procedure was then followed as in example 1. IV=0.66 dl/g $T_g$ 84° C.; $T_c$ 213° C.; $T_m$ 266° C.

Example 19—Synthesis of pH-O-pH-Co—{Ch$_2$}n-CO-pH-O-pH (EKXKE) Monomers Synthesis of 1,10-Bis(4-Phenoxybenzoyl)Decane; pH-O-pH-Co—{Ch$_2$}$_{10}$—Co-pH-O-pH To a 5 liter jacketed reaction vessel fitted with a mechanical stirrer, thermometer and nitrogen inlet/gas outlet was added 1500 ml of dry dichloromethane (DCM). All additions were carried out under a dry nitrogen atmosphere. After cooling the DCM to −20° C. anhydrous aluminium chloride (208 g; 1.56M) which was added accompanied by a slight exotherm. After allowing the temperature of the slurry to fall back to −20° C., diphenyl ether (208 g; 1.56M) was added slowly to the slurry whilst maintaining the temperature of the slurry below −10° C. When the diphenyl ether had been added, dodecanedioyl dichloride (174 g; 0.65M) dissolved in 500 ml of dry DCM, was added whilst maintaining the reaction of the slurry below −15° C. Upon completion of the addition of the dodecanedioyl dichloride the temperature of the slurry was raised to 0° C. over 1 hour and the nitrogen purge replaced by a gas outlet attached to an acid gas scrubber. During this time the solution became dark orange and hydrogen chloride gas was evolved. After gas evolution had ceased, about 3 hours, the reaction temperature was raised to +20° C. over another 2 hours. The crude product was isolated from the dark orange reaction mixture by carefully pouring the mixture into 5000 ml of ice/water with stirring. Care needs to be taken as this step is highly exothermic. After complete decomplexation the mixture consisted of a white paste and water. After decanting off the aqueous layer the paste was slurried in 2500 ml of methanol with stirring. The white product was separated from the methanol by filtration. The white product was returned to another 2000 ml of methanol and re-filtered to ensure complete removal of excess diphenyl ether. After rinsing the product on the filter with 1000 ml of fresh methanol the white powder was dried overnight at +50° C. The product was purified to polymerisation grade by crystallisation from methylcyclohexane (125 g/liter) to give a pure white crystalline product that was dried overnight under vacuum at +50° C.

Yield of crude product: 347 g; Yield of pure product: 322 g (92%)

The purity of the product was 99.93M/% as determined by DSC. Melting point: 104-105° C.

The structure of the product was confirmed by $^1$H, $^{13}$C NMR spectroscopy and mass spectrometer.

Other EK-{CH$_2$}n-KE monomers were prepared in a similar fashion, see table below.

| Monomer | Melting Point/° C. | DSC Purity/% | Yield/% |
|---|---|---|---|
| EK-3-KE | 100 | 99+ | ~90+ |
| EK-4-KE | 125.5 | 99+ | ~90+ |
| EK-5-KE | 79 and 82.2 | Gave high molecular weight polymer | ~90+ |
| EK-6-KE | 124 | 99+ | ~90+ |
| EK-8-KE | 107.5 | 99+ | ~90+ |
| EK-10-KE | 105.3 | 99+ | ~90+ |
| EK-Cyclohexyl-KE | 182.5 (major); 217.3 (minor) Possible cis/trans isomers | Gave high molecular weight polymer | ~90+ |
| EK-12-KE | | 99+ | ~90+ |
| EK-18-KE | | | |

What is claimed is:

1. A process for producing a polymer, said process comprising polymerizing a monomer system comprising a compound of formula: Ar—O—Ar—C(=O)—X—C(=O)—Ar—O—Ar in a reaction medium comprising a Lewis acid, wherein:
   X is an aliphatic moiety,
   and
   Ar is an aromatic moiety.

2. The process as claimed in claim 1, wherein the reaction medium further comprises a dielectrophile.

3. The process as claimed in claim 2, wherein said dielectrophile is a compound of formula: L-(O=)C—Ar—C(=O)-L, wherein L is a leaving group.

4. The process as claimed in claim 1, wherein X is selected from cyclohexyl (Cy) and —{CH$_2$}$_n$—, wherein n is an integer from 1 to 100.

5. The process as claimed in claim 1, wherein the compound of formula: Ar—O—Ar—C(=O)—X—C(=O)—Ar—O—Ar is polymerized in presence of a controlling agent.

6. The process as claimed in claim 5, wherein the controlling agent is a Lewis base.

7. The process as claimed in claim 5, wherein the controlling agent is an aromatic carboxylic acid, aromatic sulphonic acid or a derivative thereof.

8. The process as claimed in claim 7, wherein the controlling agent is selected from the group consisting of:
   (i) Ar(COOG)$_y$;
   (ii) Ar(SO$_3$G)$_y$;
   (iii) (ArCOO$^-$)$_z$(Met)$^{z+}$; and
   (iv) (ArSO$_3$$^-$)$_z$(Met)$^{z+}$
wherein Ar is an aromatic group compatible with the remaining components of the reaction medium;
each G independently is a hydrogen atom or an organic group (R);
each y independently is 1, 2 or 3;
each (Met) independently is a metal ion; and
each z independently is an integer equal to the charge on the metal ion (Met)$^{z+}$.

9. The process as claimed in claim 7, wherein the controlling agent is benzoic acid.

10. The process as claimed in claim 5, wherein an amount of the controlling agent is from 0.25 to 4 equivalents per equivalent of acid halide groups.

11. The process as claimed in claim 1, wherein the aromatic moiety (Ar) is independently selected from the group consisting of substituted and unsubstituted mononuclear aromatic moieties and substituted and unsubstituted polynuclear aromatic moieties.

12. The process as claimed in claim 1, wherein the compound of formula: Ar—O—Ar—C(=O)—X—C(=O)—Ar—O—Ar is polymerized with a comonomer.

13. The process as claimed in claim 1, wherein the compound of formula: Ar—O—Ar—C(=O)—X—C(=O)—Ar—O—Ar is polymerized in presence of a capping agent comprising —$NR_2$, —NRH or a protected amine group.

* * * * *